United States Patent
Hagar et al.

(10) Patent No.: US 11,285,088 B2
(45) Date of Patent: Mar. 29, 2022

(54) SPHERICAL SILICA PARTICLE SIZE FOR RDA CONTROL

(71) Applicant: Evonik Operations GmbH, Essen (DE)

(72) Inventors: William J. Hagar, Perryville, MD (US); Terry W. Nassivera, Gambrills, MD (US); Karl W. Gallis, Perryville, MD (US)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 16/642,069

(22) PCT Filed: Aug. 28, 2018

(86) PCT No.: PCT/EP2018/073097
§ 371 (c)(1),
(2) Date: Feb. 26, 2020

(87) PCT Pub. No.: WO2019/042975
PCT Pub. Date: Mar. 7, 2019

(65) Prior Publication Data
US 2020/0206107 A1  Jul. 2, 2020

Related U.S. Application Data

(60) Provisional application No. 62/684,082, filed on Jun. 12, 2018, provisional application No. 62/551,259, filed on Aug. 29, 2017.

(51) Int. Cl.
*A61K 8/25* (2006.01)
*A61K 8/02* (2006.01)

(52) U.S. Cl.
CPC ............... *A61K 8/25* (2013.01); *A61K 8/025* (2013.01)

(58) Field of Classification Search
None
See application file for complete search history.

(56) References Cited

U.S. PATENT DOCUMENTS 3,893,840 A * 7/1975 Wason ............... C09C 1/30
106/492
3,960,586 A * 6/1976 Wason ............... A61Q 11/00
106/492

(Continued)

FOREIGN PATENT DOCUMENTS

WO  WO-9005113 A1 * 5/1990  ............. A61Q 11/00
WO  WO 96/34592 A1  11/1996

(Continued)

OTHER PUBLICATIONS

Matthias Epple, Frederic Meyer, and Joachim Enax. "A Critical Review of Modern Concepts for Teeth Whitening." Dentistry Journal, vol. 7, Issue 79, 2019, pp. 1-13. (Year: 2019).*

(Continued)

*Primary Examiner* — Isaac Shomer
(74) *Attorney, Agent, or Firm* — Oblon, McClelland, Maier & Neustadt, L.L.P.

(57) ABSTRACT

Silica particles having a d50 median particle size of at least 6 μm, a ratio of (d90–d10)/d50 from 1.1 to 2.4, a RDA at 20 wt. % loading from 40 to 200, and a sphericity factor (S80) of at least 0.9, are disclosed, as well as methods for making these silica particles, and dentifrice compositions containing the silica particles.

21 Claims, 13 Drawing Sheets

(56) References Cited

U.S. PATENT DOCUMENTS

| | | | |
|---|---|---|---|
| 4,340,583 A | | 7/1982 | Wason |
| 4,420,312 A | | 12/1983 | Wason |
| 4,421,527 A | | 12/1983 | Wason |
| 5,603,920 A | * | 2/1997 | Rice .................. A61K 8/25 424/49 |
| 5,651,958 A | | 7/1997 | Rice |
| 5,869,028 A | * | 2/1999 | McGill ................ A61K 8/25 424/49 |
| 6,294,155 B1 | * | 9/2001 | Thomas .............. A61K 8/25 423/339 |
| 6,419,174 B1 | * | 7/2002 | McGill ................ A61K 8/25 423/335 |
| 6,616,916 B1 | | 9/2003 | Karpe et al. |
| 6,946,119 B2 | | 9/2005 | Gallis et al. |
| 7,255,852 B2 | | 8/2007 | Gallis et al. |
| 7,438,895 B2 | | 10/2008 | Gallis |
| 8,609,068 B2 | * | 12/2013 | Hagar .................. A61K 6/70 424/49 |
| 8,945,517 B2 | | 2/2015 | Hagar et al. |
| 9,028,605 B2 | | 5/2015 | Hagar et al. |
| 9,186,307 B2 | | 11/2015 | Gallis et al. |
| 9,327,988 B2 | | 5/2016 | Hagar et al. |
| 9,617,162 B2 | | 4/2017 | Hagar et al. |
| 10,287,438 B2 | | 5/2019 | Nassivera et al. |
| 10,328,002 B2 | * | 6/2019 | Dolan .................. A61K 8/19 |
| 2006/0110338 A1 | * | 5/2006 | McGill ................ C01B 33/193 424/49 |
| 2006/0140878 A1 | * | 6/2006 | Cornelius ............. A61Q 11/00 424/49 |
| 2008/0160053 A1 | | 7/2008 | McGill et al. |
| 2011/0206746 A1 | * | 8/2011 | Hagar ............. B01J 20/28059 424/401 |
| 2014/0072634 A1 | | 3/2014 | Hagar et al. |
| 2014/0272012 A1 | | 9/2014 | Gallis et al. |
| 2015/0086463 A1 | | 3/2015 | Hagar et al. |
| 2016/0038387 A1 | | 2/2016 | Gallis et al. |
| 2016/0214865 A1 | | 7/2016 | Hagar et al. |
| 2017/0087066 A1 | | 3/2017 | Nassivera et al. |
| 2020/0109056 A1 | | 4/2020 | Gallis et al. |

FOREIGN PATENT DOCUMENTS

| | | |
|---|---|---|
| WO | WO 02/15858 A1 | 2/2002 |
| WO | WO 2011/106289 A2 | 9/2011 |
| WO | 2019042887 A1 | 3/2019 |
| WO | 2019238777 A1 | 12/2019 |

OTHER PUBLICATIONS

International Search Report and Written Opinion dated Oct. 29, 2018 in PCT/EP2018/073097 filed on Aug. 28, 2018.

"Periodic table of the elements," Chemical and Engineering News, vol. 63, No. 5, Feb. 1985, p. 27.

Brunauer, S. et al., "Adsorption of Gases in Multimolecular Layers," J. Am. Chem. Soc., vol. 60, Feb. 1938, pp. 309-319.

Stookey, G. K. et al., "In vitro Removal of Stain with Dentifrices," J. Dental Res., vol. 61, Feb. 1982, pp. 1236-1239.

Hefferren, J. J., "A Laboratory Method for Assessment of Dentifrice Abrasivity," Journal of Dental Res., vol. 55, No. 4, Jul.-Aug. 1976, pp. 563-573.

* cited by examiner

SPHERICAL SILICA PARTICLE SIZE FOR RDA CONTROL

BACKGROUND OF THE INVENTION

Relative dentin abrasion (RDA) is a test that is used to set safety limits for toothpaste and other dentifrice compositions. The RDA test involves measuring the loss of dentin after brushing with a test toothpaste formulation relative to the control calcium pyrophosphate (set to 100).

Spherical silica particles, as compared to traditional non-spherical and irregularly shaped silica particles, have certain properties (such as low Einlehner abrasion) that are beneficial for their use in toothpaste and other dentifrice applications. However, it would be advantageous for these spherical silica materials also to have improved RDA performance. Accordingly, it is to this end that the present invention is principally directed.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Silica particles with reduced Relative Dentin Abrasion (RDA) are disclosed and described herein. In accordance with an aspect of this invention, such silica particles can have (i) a d50 median particle size of greater than or equal to about 6 µm, (ii) a ratio of (d90−d10)/d50 in a range from about 1.1 to about 2.4, (iii) a RDA at 20 wt. % loading in a range from about 40 to about 200, and (iv) a sphericity factor ($S_{80}$) of greater than or equal to about 0.9. These silica particles have a spherical shape or morphology, and can be produced using a continuous loop reactor process.

Also disclosed herein are dentifrice compositions containing the spherical silica particles, typically at amounts in the 0.5-50 wt. % range, and more often, in the 5-35 wt. % range.

Processes for producing the silica particles also are provided herein, and one such process can comprise (a) continuously feeding a mineral acid and an alkali metal silicate into a loop reaction zone comprising a stream of liquid medium, wherein at least a portion of the mineral acid and the alkali metal silicate react to form the silica particles in the liquid medium of the loop reaction zone, (b) continuously recirculating the liquid medium through the loop reaction zone, and (c) continuously discharging from the loop reaction zone a portion of the liquid medium comprising the silica particles. Beneficially, steps (a)-(c) can be conducted under low shear or no shear conditions, unexpectedly resulting in rounder and more spherical particle morphology. For instance, the loop reaction zone can be configured without a stator screen or the loop reaction zone can comprise a stator screen with openings greater than 3 $mm^2$ in cross sectional area. Additionally or alternatively, the shear frequency in the loop reaction zone can be less than 1,000,000 interactions/min.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

DEFINITIONS

Figure 1:
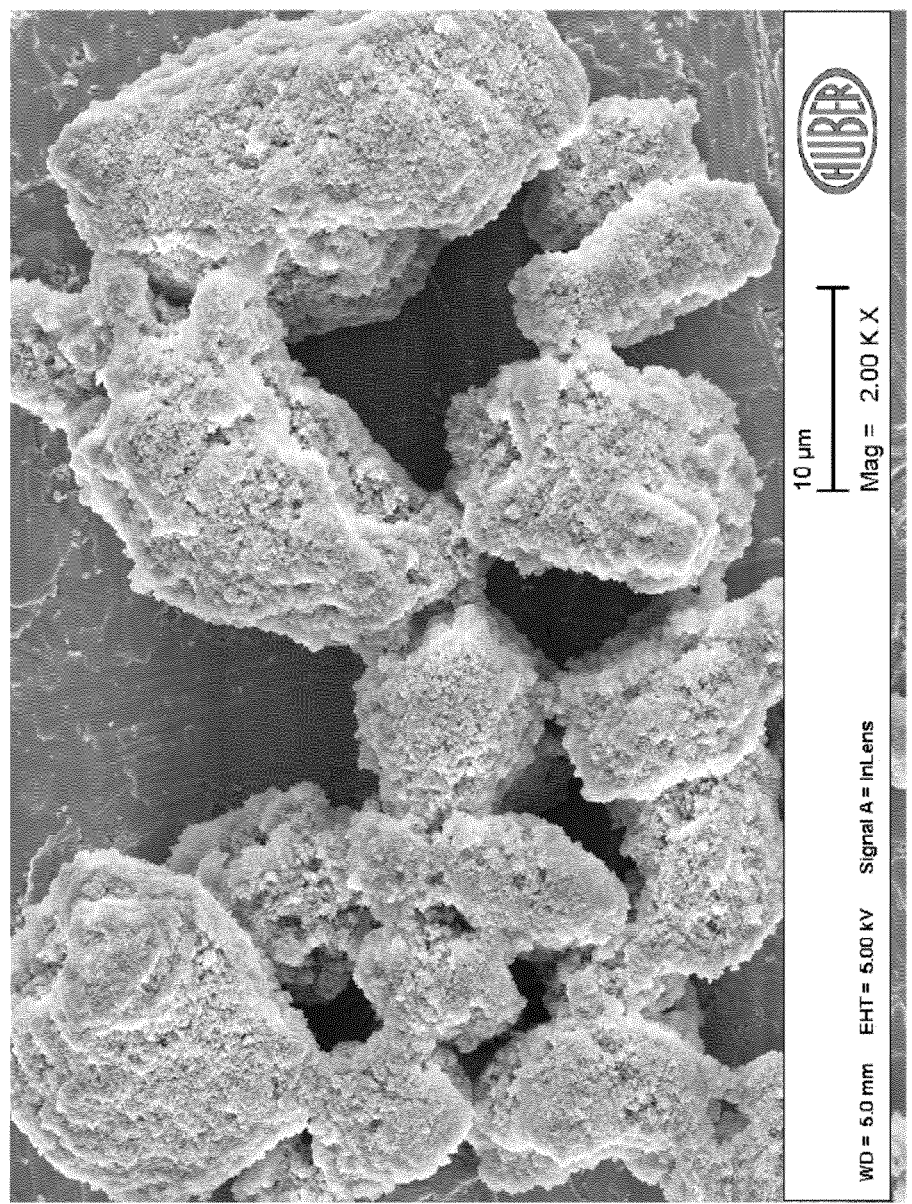
FIG. 1 is a Scanning Electron Micrograph of the silica of Example 1A.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features can be envisioned. For each and every aspect and each and every feature disclosed herein, all combinations that do not detrimentally affect the designs, compositions, processes, or methods described herein are contemplated and can be interchanged, with or without explicit description of the particular combination. Accordingly, unless explicitly recited otherwise, any aspect or feature disclosed herein can be combined to describe inventive designs, compositions, processes, or methods consistent with the present disclosure.

While compositions and methods are described herein in terms of "comprising" various components or steps, the compositions and methods can also "consist essentially of" or "consist of" the various components or steps, unless stated otherwise.

The terms "a," "an," and "the" are intended to include plural alternatives, e.g., at least one, unless otherwise specified.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, and so forth.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein. As a representative example, the BET surface area of the silica particles can be in certain ranges in various aspects of this invention. By a disclosure that the BET surface area is in a range from about 20 to about 100 $m^2/g$, the intent is to recite that the surface area can be any surface area within the range and, for example, can be equal to about 20, about 30, about 40, about 50, about 60, about 70, about 80, about 90, or about 100 $m^2/g$. Additionally, the surface area can be within any range from about 20 to about 100 $m^2/g$ (for example, from about 45 to about 85 $m^2/g$), and this also includes any combination of ranges between about 20 and about 100 $m^2/g$ (for example, the surface area can be in a range from about 20 to about 50 $m^2/g$, or from about 70 to about 90 $m^2/g$). Likewise, all other ranges disclosed herein should be interpreted in a manner similar to this example.

DETAILED DESCRIPTION OF THE INVENTION

Disclosed herein are generally spherical silica particles that can be characterized by (i) a d50 median particle size of greater than or equal to about 6 μm, (ii) a ratio of (d90–d10)/d50 in a range from about 1.1 to about 2.4, (iii) a RDA at 20 wt. % loading in a range from about 40 to about 200, and (iv) a sphericity factor ($S_{80}$) of greater than or equal to about 0.9. Methods of making these spherical silica particles, and dentifrice compositions containing the spherical particles, also are disclosed and described herein.

Spherical Silica Particles

Consistent with aspects of the present invention, spherical silica particles with improved RDA performance can have the following characteristics: (i) a d50 median particle size of greater than or equal to about 6 μm, (ii) a ratio of (d90–d10)/d50 in a range from about 1.1 to about 2.4, (iii) a RDA at 20 wt. % loading in a range from about 40 to about 200, and (iv) a sphericity factor ($S_{80}$) of greater than or equal to about 0.9. In further aspects, such silica particles consistent with the present invention also can have any of the characteristics or properties provided below, and in any combination.

In an aspect, the spherical silica particles can have a relatively large average particle size. Often, the median particle size (d50) and/or mean particle size (average) can fall within a range from about from about 6 to about 30, from about 6 to about 25 in a particular aspect, from about 6 to about 20 in a particular aspect, from about 7 to about 25 in a particular aspect, from about 7 to about 20 in a particular aspect, and from about 7 to about 18 μm in a more particular aspect. In another aspect, the median particle size (d50) and/or mean particle size (average) can fall within a range from about 8 to about 25, from about 8 to about 20 in a particular aspect, from about 8 to about 18 in a particular aspect, and from about 8 to about 15 μm in a more particular aspect. Other appropriate ranges for the mean and median particle sizes are readily apparent from this disclosure.

The spherical particles also have a very narrow particle size distribution, which can be quantified by the ratio of (d90–d10)/d50. A lower value for the ratio indicates a narrower particle size distribution, while a larger value for the ratio indicates a broader particle size distribution. Generally, the spherical particles disclosed herein can be characterized by a ratio of (d90–d10)/d50 in a range from about 1.1 to about 2.4. In one aspect, the ratio of (d90–d10)/d50 can be in a range from about 1.1 to about 2.2, while in another aspect, the ratio of (d90–d10)/d50 can be in a range from about 1.1 to about 2. Yet, in another aspect, the ratio of (d90–d10)/d50 can be in a range from about 1.2 to about 2.4, while in still another aspect, the ratio of (d90–d10)/d50 can be in a range from about 1.2 to about 2.2, and from about 1.2 to about 2 in a more particular aspect. Other appropriate ranges for the ratio of (d90–d10)/d50 are readily apparent from this disclosure.

The Relative Dentin Abrasion (RDA) test is typically performed to confirm that a dentifrice composition, e.g., toothpaste, is safe for consumer use, with the upper limit of the test set at 250. Unexpectedly, the results provided herein demonstrate that, for the spherical silica particles consistent with this invention, the RDA generally decreases as the median particle size (d50) and/or mean particle size (average) increases. The spherical silica particles can be characterized by a RDA at 20 wt. % loading in a range from about 40 to about 200 in one aspect of this invention, and from about 50 to about 190 in another aspect. Other illustrative and non-limiting ranges for the RDA at 20 wt. % loading can include from about 70 to about 200, from about 70 to about 170 in a particular aspect, from about 85 to about 180 in a particular aspect, and from about 100 to about 160 in a more particular aspect. Other appropriate ranges for the RDA are readily apparent from this disclosure.

The sphericity of the spherical silica particles can be quantified by a sphericity factor ($S_{80}$), which is typically greater than or equal to about 0.85, greater than or equal to about 0.88 in a particular aspect, and greater than or equal to about 0.9 in a more particular aspect. The sphericity factor ($S_{80}$) is determined as follows. An SEM image of the silica particle sample is magnified 20,000 times, which is representative of the silica particle sample, and is imported into photo imaging software, and the outline of each particle (two-dimensionally) is traced. Particles that are close in proximity to one another but not attached to one another should be considered separate particles for this analysis. The outlined particles are then filled in with color, and the image is imported into particle characterization software (e.g., IMAGE-PRO PLUS available from Media Cybernetics, Inc., Bethesda, Md.) capable of determining the perimeter and area of the particles. Sphericity of the particles can then be calculated according to the equation, Sphericity=(perimeter)$^2$ divided by (4π×area), wherein perimeter is the software measured perimeter derived from the outlined trace of the particles, and wherein area is the software measured area within the traced perimeter of the particles.

The sphericity calculation is performed for each particle that fits entirely within the SEM image. These values are then sorted by value, and the lowest 20% of these values are discarded. The remaining 80% of these values are averaged to obtain the sphericity factor ($S_{80}$). Additional information on sphericity can be found in U.S. Pat. Nos. 8,945,517 and 8,609,068, incorporated herein by reference in their entirety.

In one aspect of this invention, the spherical silica particles can have a sphericity factor ($S_{80}$) greater than or equal to about 0.85, greater than or equal to about 0.88 in another aspect, and greater than or equal to about 0.9 in a more particular aspect. Yet, in another aspect, the spherical silica particles can be characterized by a sphericity factor ($S_{80}$) greater than or equal to about 0.92, and in still another aspect, the silica particles can be characterized by a sphericity factor ($S_{80}$) greater than or equal to about 0.94. As one of skill in the art would readily recognize, a 3-dimensional sphere (or 2-dimensional circle) will have a sphericity factor ($S_{80}$) equal to 1.

The spherical silica particles can have any suitable surface area, generally a BET surface area ranging from about 10 to about 200 $m^2/g$. Often, the BET surface area can fall within a range from about 20 to about 200, from about 20 to about 180 in a particular aspect, and from about 20 to about 160 $m^2/g$ in a more particular aspect. In further aspects, the BET surface area can be in a range from about 20 to about 130, from about 20 to about 100 in a particular aspect, from about 30 to about 180 in a particular aspect, from about 30 to about 160 in a particular aspect, from about 30 to about 100 in a particular aspect, from about 40 to about 180 in a particular aspect, and from about 40 to about 80 $m^2/g$ in a more particular aspect. Other appropriate ranges for the BET surface area are readily apparent from this disclosure.

Additionally, the spherical silica particles can be less abrasive, as reflected by an Einlehner abrasion value ranging from about 0.25 to about 8 mg lost/100,000 revolutions. For instance, the Einlehner abrasion value can be in a range from about 0.5 to about 7; alternatively, from about 0.5 to about 5; or alternatively, from about 0.75 to about 4 mg lost/100,000 revolutions. Other appropriate ranges for the Einlehner abrasion value are readily apparent from this disclosure.

While not being limited thereto, the spherical silica particles can have a pack density in a range from about 25 to about 65 $lb/ft^3$ in one aspect of the invention. In another aspect, the pack density can be in a range from about 35 to about 60 $lb/ft^3$, from about 40 to about 65 $lb/ft^3$ in a particular aspect, and from about 40 to about 60 $lb/ft^3$ in a more particular aspect. In yet another aspect, the pack density can be in the range from about 35 to about 65 $lb/ft^3$. Other appropriate ranges for the pack density are readily apparent from this disclosure.

Generally, the silica particles can have an oil absorption in a range from about 30 to about 115 cc/100 g, from about 30 to about 90 cc/100 g in a particular aspect, and from about 30 to about 80 cc/100 g in a more particular aspect. Additionally or alternatively, the spherical silica particles can have a relatively narrow particle size distribution, with a weight percent of 325 mesh residue (amount retained in a 325 mesh sieve) generally less than or equal to about 1.2 wt. %. In some aspects, the 325 mesh residue can be less than or equal to about 1 wt. %, less than or equal to about 0.75 wt. % in a particular aspect, less than or equal to about 0.5 wt. % in a particular aspect, and less than or equal to about 0.3 wt. % in a more particular aspect. Other appropriate ranges for the oil absorption and the 325 mesh residue are readily apparent from this disclosure.

In these and other aspects, any of the spherical silica particles can be amorphous, can be synthetic, or can be both amorphous and synthetic. Moreover, the spherical silica particles can comprise precipitated silica particles in particular aspects of this invention, although not limited thereto.

The spherical silica particles also can be described by their Pellicle Cleaning Ratio (PCR), which is a measure of the cleaning characteristics of a dentifrice composition containing the silica particles. The silica particles can be characterized by a PCR at 20 wt. % loading in a range about 50 to about 110 in one aspect, from about 70 to about 110 in another aspect, from about 80 to about 110 in another aspect, from about 60 to about 100 in yet another aspect, and from about 70 to about 105 in still another aspect. The PCR/RDA ratio (at 20 wt. % loading) often can be from about 0.5:1 to about 1.3:1 in one aspect, from about 0.5:1 to about 1.2:1 in another aspect, from about 0.5:1 to about 1:1 in yet another aspect, and from about 0.5:1 to about 0.7:1 in still another aspect.

Processes for Producing Silica Particles

The spherical silica particles disclosed herein are not limited to any particular synthesis procedure. However, in order to achieve the desired sphericity, a continuous loop reactor process can be utilized to form the spherical silica particles. A general process and associated reactor system (which can include a continuous loop of one or more loop reactor pipes) are described in U.S. Pat. Nos. 8,945,517 and 8,609,068, incorporated herein by reference in their entirety. Appropriate modifications, as described herein, are made to the general process and reactor system to improve particle sphericity.

In general, the continuous loop process involves (a) continuously feeding a mineral acid and an alkali metal silicate into a loop reaction zone comprising a stream of liquid medium (water-based), wherein at least a portion of the mineral acid and the alkali metal silicate react to form a silica product (e.g., the silica particles) in the liquid medium of the loop reaction zone, (b) continuously recirculating the liquid medium through the loop reaction zone, and (c) continuously discharging from the loop reaction zone a portion of the liquid medium comprising the silica product. In particular aspects of this invention, steps (a)-(c) are performed simultaneously.

Typically, although not required, the feed locations of the mineral acid and the alkali metal silicate into the loop reaction zone are different, and the total volumetric feed rate of acid and silicate can be proportional to, and often equal to, the volumetric discharge rate of the liquid medium containing the silica product. All or substantially all of the contents (greater than 95 wt. %) within the loop reaction zone generally are recirculated. The liquid medium, for instance, can be recirculated through the loop reaction zone at a rate ranging from about 50 vol. % per minute (the recirculation rate, per minute, is one-half of the total volume of the liquid medium in the loop reaction zone) to about 1000 vol. % per minute (the recirculation rate, per minute, is ten times the total volume of the liquid medium in the loop reaction zone), or from about 75 vol. % per minute to about 500 vol. % per minute. Representative and non-limiting ranges for the volumetric recirculation rate of the liquid medium through the loop reaction zone include from about 15 L/min to about 150 L/min in one aspect, and from about 60 L/min to about 100 L/min in another aspect.

The loop reaction zone can comprise a continuous loop of one or more loop reactor pipes. Thus, for example, the process can be conducted—continuously—in a single loop reactor. Any suitable pump can be used to utilized to recirculate the liquid medium through the loop reaction zone. The temperature of the liquid medium in the loop reaction zone can be controlled using any suitable technique or control system.

In one aspect, the alkali metal silicate can comprise sodium silicate, and the mineral acid can comprise sulfuric acid, hydrochloric acid, nitric acid, phosphoric acid, or a combination thereof. In another aspect, the alkali metal silicate can comprise sodium silicate, and the mineral acid can comprise an acidic solution of aluminum sulfate. In these and other aspects, the resultant silica product can comprise precipitated silica or precipitated sodium aluminosilicate. The pH of the liquid medium being recirculated through the loop reaction zone can range from about 2.5 to about 10, but more often ranges from about 6 to about 10, from about 6.5 to about 8.5 in a particular aspect, and from about 7 to about 8 in a more particular aspect.

In order to promote increased sphericity, the continuous loop process for producing the silica product can be performed under low shear or no shear conditions. For instance, the stator screen on the loop reactor mixing device can be removed for low shear or no shear operation. Alternatively, a stator design having large openings (e.g., slots, circular holes, square holes, etc.) can be used, such that the stator screen in the loop reaction zone has openings greater than 3 $mm^2$ in cross sectional area (e.g., greater than 10 $mm^2$ in one aspect, greater than 50 $mm^2$ in another aspect, greater than 100 $mm^2$ in yet another aspect, greater than 500 $mm^2$ in still another aspect, etc., in cross sectional area), for low shear or no shear operation. Further, the mixer rpm's can be reduced to less than 3000 rpm, less than 2500 rpm in a particular aspect, and less than 2000 rpm in a more particular aspect, to reduce shear in the loop reaction zone. Additionally, the recirculation step of the process—step (b)—can be conducted at a relatively high temperature, often ranging from about 85 to about 100° C., from about 90 to about 100° C. in another aspect, and from about 88 to about 98° C. in yet another aspect. Additionally or alternatively, for low shear or no shear conditions, the shear frequency in the loop reaction zone can be less than 1,000,000 interactions/min in one aspect, less than 750,000 interactions/min in another aspect, less than 500,000 interactions/min in yet another aspect, and less than 250,000 interactions/min in still another aspect. The shear frequency is defined as the number of interactions between the flow from the rotor and the stator: rpm×$N_R$×$N_S$, where rpm is the mixer/rotor revolutions per minute, $N_R$ is the number of blades/teeth on the rotor, and $N_S$ is the number of holes/slots (openings) on the stator. Thus, at 2700 rpm for a 4-blade rotor, 10 large round holes on the stator would equate to 108,000 interactions/min (low shear), whereas a stator with 400 small holes would equate to 4,320,000 interactions/minute (high shear).

While not being limited thereto, the pH of the silica particles after discharge from the loop reaction zone often can be adjusted to within a range from about 5 to about 8.5, and in some cases, from about 5.5 to about 8 in a particular aspect, and from about 5.5 to about 7.5 in a more particular aspect, for suitability in end-use dentifrice and other applications.

After the pH adjustment step, and optionally, the processes disclosed herein can further include a filtering step to isolate the silica particles, a washing step to wash the silica particles, a drying step (e.g., spray drying) to dry the silica particles, or any combination of the filtering, washing, and drying steps, and performed in any suitable sequence.

Dentifrice Compositions

The spherical silica particles can be used in any suitable composition and for any suitable end-use application. Often, the silica particles can be used in oral care applications, such as in a dentifrice composition. The dentifrice composition can contain any suitable amount of the silica particles, such as from about 0.5 to about 50 wt. %, from about 1 to about 50 wt. % in a particular aspect, from about 5 to about 35 wt. % in a particular aspect, from about 10 to about 40 wt. % in a particular aspect, and from about 10 to about 30 wt. % in a more particular aspect, of the spherical silica particles. These weight percentages are based on the total weight of the dentifrice composition.

The dentifrice composition can be in any suitable form, such as a liquid, powder, or paste. In addition to the silica particles, the dentifrice composition can contain other ingredients or additives, non-limiting examples of which can include a humectant, a solvent, a binder, a therapeutic agent, a chelating agent, a thickener other than the silica particles, a surfactant, an abrasive other than the silica particles, a sweetening agent, a colorant, a flavoring agent, a preservative, and the like, as well as any combination thereof.

Humectants serve to add body or "mouth texture" to a dentifrice as well as preventing the dentifrice from drying out. Suitable humectants include polyethylene glycol (at a variety of different molecular weights), propylene glycol, glycerin (glycerol), erythritol, xylitol, sorbitol, mannitol, lactitol, and hydrogenated starch hydrolyzates, and mixtures thereof. In some formulations, humectants are present in an amount from about 20 to about 50 wt. %, based on the weight of the dentifrice composition.

A solvent can be present in the dentifrice composition, at any suitable loading, and usually the solvent comprises water. When used, water is preferably deionized and free of impurities, can be present in the dentifrice at loadings from 5 to about 70 wt. %, and from about 5 to about 35 wt. % in another aspect, based on the weight of dentifrice composition.

Therapeutic agents also can be used in the compositions of this invention to provide for the prevention and treatment of dental caries, periodontal disease, and temperature sensitivity, for example. Suitable therapeutic agents can include, but are not limited to, fluoride sources, such as sodium fluoride, sodium monofluorophosphate, potassium monofluorophosphate, stannous fluoride, potassium fluoride, sodium fluorosilicate, ammonium fluorosilicate and the like; condensed phosphates such as tetrasodium pyrophosphate, tetrapotassium pyrophosphate, disodium dihydrogen pyrophosphate, trisodium monohydrogen pyrophosphate; tripolyphosphates, hexametaphosphates, trimetaphosphates and pyrophosphates; antimicrobial agents such as triclosan, bisguanides, such as alexidine, chlorhexidine and chlorhexidine gluconate; enzymes such as papain, bromelain, glucoamylase, amylase, dextranase, mutanase, lipases, pectinase, tannase, and proteases; quaternary ammonium compounds, such as benzalkonium chloride (BZK), benzethonium chloride (BZT), cetylpyridinium chloride (CPC), and domiphen bromide; metal salts, such as zinc citrate, zinc chloride, and stannous fluoride; sanguinaria extract and sanguinarine; volatile oils, such as eucalyptol, menthol, thymol, and methyl salicylate; amine fluorides; peroxides and the like. Therapeutic agents can be used in dentifrice formulations singly or in combination, and at any therapeutically safe and effective level or dosage.

Thickening agents are useful in the dentifrice compositions to provide a gelatinous structure that stabilizes the toothpaste against phase separation. Suitable thickening agents include silica thickener; starch; glycerite of starch; gums such as gum karaya (sterculia gum), gum tragacanth, gum arabic, gum ghatti, gum acacia, xanthan gum, guar gum and cellulose gum; magnesium aluminum silicate (Veegum); carrageenan; sodium alginate; agar-agar; pectin; gelatin; cellulose compounds such as cellulose, carboxymethyl cellulose, hydroxyethyl cellulose, hydroxypropyl cellulose, hydroxymethyl cellulose, hydroxymethyl carboxypropyl cellulose, methyl cellulose, ethyl cellulose, and sulfated cellulose; natural and synthetic clays such as hectorite clays; and mixtures thereof. Typical levels of thickening agents or binders are up to about 15 wt. % of a toothpaste or dentifrice composition.

Useful silica thickeners for utilization within a toothpaste composition, for example, include, as a non-limiting example, an amorphous precipitated silica such as ZEODENT 165 silica. Other non-limiting silica thickeners include ZEODENT 153, 163 and/or 167 and ZEOFREE, 177, and/or 265 silica products, all available from J. M. Huber Corporation.

Surfactants can be used in the dentifrice compositions of the invention to make the compositions more cosmetically acceptable. The surfactant is preferably a detersive material which imparts to the composition detersive and foaming properties. Suitable surfactants are safe and effective amounts of anionic, cationic, nonionic, zwitterionic, amphoteric and betaine surfactants such as sodium lauryl sulfate, sodium dodecyl benzene sulfonate, alkali metal or ammonium salts of lauroyl sarcosinate, myristoyl sarcosinate, palmitoyl sarcosinate, stearoyl sarcosinate and oleoyl sarcosinate, polyoxyethylene sorbitan monostearate, isostearate and laurate, sodium lauryl sulfoacetate, N-lauroyl sarcosine, the sodium, potassium, and ethanolamine salts of N-lauroyl, N-myristoyl, or N-palmitoyl sarcosine, polyethylene oxide condensates of alkyl phenols, cocoamidopropyl betaine, lauramidopropyl betaine, palmityl betaine and the like. Sodium lauryl sulfate is a preferred surfactant. The surfactant is typically present in the compositions of the present invention in an amount from about 0.1 to about 15 wt. %, from about 0.3 to about 5 wt. % in a particular aspect, and from about 0.3 to about 2.5 wt. % in a more particular aspect.

The disclosed silica particles can be utilized alone as the abrasive in the dentifrice composition, or as an additive or co-abrasive with other abrasive materials discussed herein or known in the art. Thus, any number of other conventional types of abrasive additives can be present within the dentifrice compositions of the invention. Other such abrasive particles include, for example, precipitated calcium carbonate (PCC), ground calcium carbonate (GCC), chalk, bentonite, dicalcium phosphate or its dihydrate forms, silica gel (by itself, and of any structure), precipitated silica, amorphous precipitated silica (by itself, and of any structure as well), perlite, titanium dioxide, dicalcium phosphate, calcium pyrophosphate, alumina, hydrated alumina, calcined alumina, aluminum silicate, insoluble sodium metaphosphate, insoluble potassium metaphosphate, insoluble magnesium carbonate, zirconium silicate, particulate thermosetting resins and other suitable abrasive materials. Such materials can be introduced into the dentifrice compositions to tailor the polishing characteristics of the target formulation.

Sweeteners can be added to the dentifrice composition (e.g., toothpaste) to impart a pleasing taste to the product. Suitable sweeteners include saccharin (as sodium, potassium or calcium saccharin), cyclamate (as a sodium, potassium or calcium salt), acesulfame-K, thaumatin, neohesperidin dihydrochalcone, ammoniated glycyrrhizin, dextrose, levulose, sucrose, mannose, and glucose.

Colorants can be added to improve the aesthetic appearance of the product. Suitable colorants include without limitation those colorants approved by appropriate regulatory bodies such as the FDA and those listed in the European Food and Pharmaceutical Directives and include pigments, such as $TiO_2$, and colors such as FD&C and D&C dyes.

Flavoring agents also can be added to dentifrice compositions. Suitable flavoring agents include, but are not limited to, oil of wintergreen, oil of peppermint, oil of spearmint, oil of sassafras, and oil of clove, cinnamon, anethole, menthol, thymol, eugenol, eucalyptol, lemon, orange and other such flavor compounds to add fruit notes, spice notes, etc. These flavoring agents generally comprise mixtures of aldehydes, ketones, esters, phenols, acids, and aliphatic, aromatic and other alcohols.

Preservatives also can be added to the compositions of the present invention to prevent bacterial growth. Suitable preservatives approved for use in oral compositions such as methylparaben, propylparaben and sodium benzoate can be added in safe and effective amounts.

Other ingredients can be used in the dentifrice composition, such as desensitizing agents, healing agents, other caries preventative agents, chelating/sequestering agents, vitamins, amino acids, proteins, other anti-plaque/anti-calculus agents, opacifiers, antibiotics, anti-enzymes, enzymes, pH control agents, oxidizing agents, antioxidants, and the like.

EXAMPLES

The invention is further illustrated by the following examples, which are not to be construed in any way as imposing limitations to the scope of this invention. Various other aspects, modifications, and equivalents thereof which, after reading the description herein, may suggest themselves to one of ordinary skill in the art without departing from the spirit of the present invention or the scope of the appended claims.

The multipoint BET surface areas disclosed herein were determined on a Micromeritics TriStar II 3020 V1.03, using the BET nitrogen adsorption method of Brunaur et al., J. Am. Chem. Soc., 60, 309 (1938).

CTAB surface areas disclosed herein were determined by absorption of CTAB (cetyltrimethylammonium bromide) on the silica surface, the excess separated by centrifugation and the quantity determined by titration with sodium lauryl sulfate using a surfactant electrode. Specifically, about 0.5 grams of the silica particles were placed in a 250-mL beaker with 100 mL CTAB solution (5.5 g/L), mixed on an electric stir plate for 1 hour, then centrifuged for 30 min at 10,000 RPM. One mL of 10% Triton X-100 was added to 5 mL of the clear supernatant in a 100-mL beaker. The pH was adjusted to 3-3.5 with 0.1 N HCl and the specimen was titrated with 0.01 M sodium lauryl sulfate using a surfactant electrode (Brinkmann SUR1501-DL) to determine the end point.

The median particle size (d50) refers to the particle size for which 50% of the sample has a smaller size and 50% of the sample has a larger size. Median particle size (d50), mean particle size (average), d90, and d10 were determined via the laser diffraction method using a Horiba LA 300 instrument. Dry particles were submitted to the instrument for analysis, and samples were de-agglomerated using ultrasonic vibration for 2 minutes.

For pour density and pack density, 20 grams of the sample were placed into a 250 mL graduated cylinder with a flat rubber bottom. The initial volume was recorded and used to calculate the pour density by dividing it into the weight of sample used. The cylinder was then placed onto a tap density machine where it was rotated on a cam at 60 RPM. The cam is designed to raise and drop the cylinder a distance of 5.715 cm once per second, until the sample volume is constant, typically for 15 min. This final volume is recorded and used to calculate the packed density by dividing it into the weight of sample used.

The Einlehner abrasion value is a measure of the hardness/abrasiveness of silica particles, and is described in detail in U.S. Pat. No. 6,616,916, incorporated herein by reference, and involves an Einlehner AT-1000 Abrader generally used as follows: (1) a Fourdrinier brass wire screen is weighed and exposed to the action of a 10% aqueous silica suspension for a fixed length of time; (2) the amount of abrasion is then determined as milligrams of brass lost from the Fourdrinier wire screen per 100,000 revolutions (mg lost/100,000 revolutions).

Oil absorption values were determined in accordance with the rub-out method described in ASTM D281 using linseed oil (cc oil absorbed per 100 g of the particles). Generally, a higher oil absorption level indicates a particle with a higher level of large pore porosity, also described as higher structure.

Water absorption values were determined with an Absorptometer "C" torque rheometer from C.W. Brabender Instruments, Inc. Approximately ⅓ of a cup of the silica sample was transferred to the mixing chamber of the Absorptometer and mixed at 150 RPM. Water then was added at a rate of 6 mL/min, and the torque required to mix the powder was recorded. As water is absorbed by the powder, the torque will reach a maximum as the powder transforms from free-flowing to a paste. The total volume of water added when the maximum torque was reached was then standardized to the quantity of water that can be absorbed by 100 g of powder. Since the powder was used on an as received basis (not previously dried), the free moisture value of the powder was used to calculate a "moisture corrected water AbC value" by the following equation.

$$\text{Water Absorption} = \frac{water absorbed (cc) + \% \text{moisture}}{(100 (g) - \% \text{moisture})/100}$$

The Absorptometer is commonly used to determine the oil number of carbon black in compliance with ASTM D 2414 methods B and C and ASTM D 3493.

The pH values disclosed herein (5% pH) were determined in an aqueous system containing 5 wt. % solids in deionized water using a pH meter.

The 325 mesh residue (wt. %) of the silica sample was measured utilizing a U.S. Standard Sieve No. 325, with 44 micron or 0.0017 inch openings (stainless steel wire cloth), by weighing a 10.0 gram sample to the nearest 0.1 gram into the cup of a 1 quart Hamilton mixer (Model No. 30), adding approximately 170 mL of distilled or deionized water, and stirring the slurry for at least 7 min. The mixture was transferred onto the 325 mesh screen and water was sprayed directly onto the screen at a pressure of 20 psig for two minutes, with the spray head held about four to six inches from the screen. The remaining residue was then transferred to a watch glass, dried in an oven at 150° C. for 15 min, then cooled, and weighed on an analytical balance.

The cleaning performance of the silica materials in a dentifrice composition is typically quantified by a Pellicle Cleaning Ratio ("PCR") value. The PCR test measures the ability of a dentifrice composition to remove pellicle film from a tooth under fixed brushing conditions. The PCR test is described in "In Vitro Removal of Stain With Dentifrice" G. K. Stookey, et al., J. Dental Res., 61, 1236-9, 1982, which is incorporated herein by reference for its teaching of PCR. PCR values are unitless.

The Relative Dentin Abrasion (RDA) of the dentifrice compositions of the invention were determined according to the method set forth by Hefferen, Journal of Dental Res., July-August 1976, 55 (4), pp. 563-573, and described in Wason U.S. Pat. Nos. 4,340,583, 4,420,312 and 4,421,527, which are each incorporated herein by reference for their teaching of RDA measurements. RDA values are unitless.

Examples 1A-2A

Irregular Silica Particles

Figure 2:
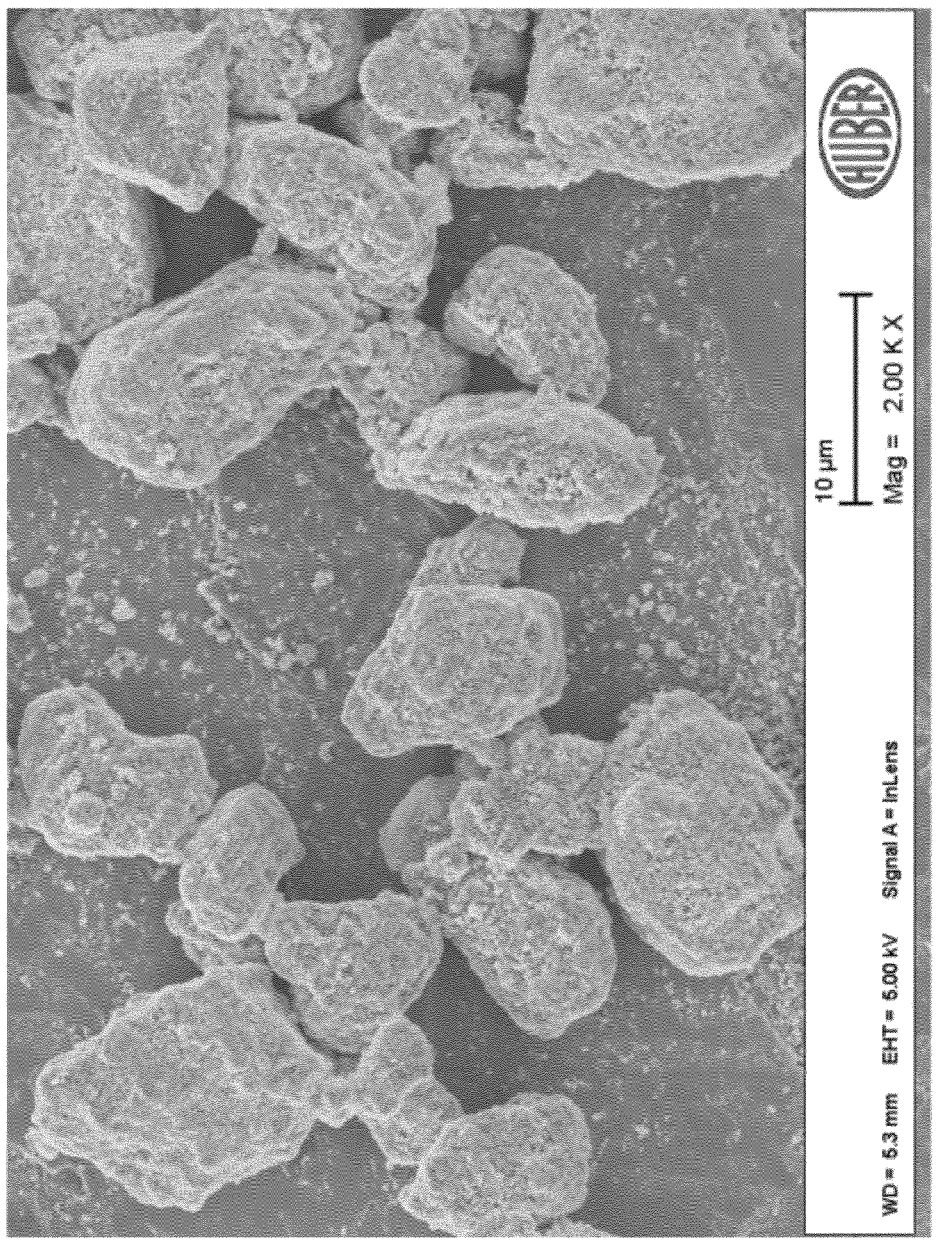
FIG. 2 is a Scanning Electron Micrograph of the silica of Example 2A.

Table I summarize certain properties of comparative silica materials 1A and 2A, which have an irregular and non-spherical particle morphology. FIG. 1 (Example 1A) and FIG. 2 (Example 2A) are SEM images that demonstrate the irregular and non-spherical shapes of the particles of Examples 1A and 2A. Examples 1A and 2A were conventional silica materials commercially available from Huber Engineered Materials.

Examples 3A-8A

Spherical Silica Particles

For Examples 3A-8A, a continuous loop reactor process (see e.g., U.S. Pat. Nos. 8,945,517 and 8,609,068) was used to produce silica particles with a spherical morphology and a tighter particle size distribution (e.g., less 325 mesh residue in the final silica product).

Figure 3:
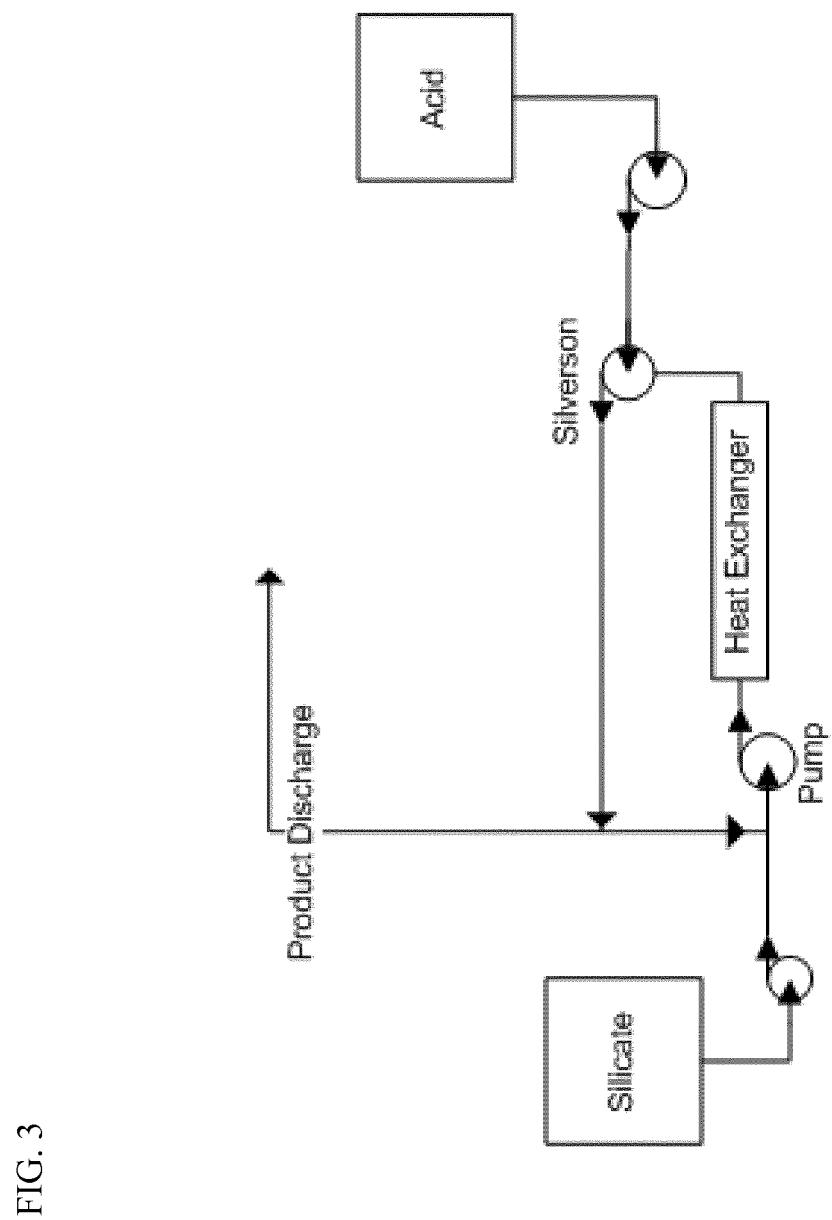
FIG. 3 is a schematic of the continuous loop reactor apparatus used to produce the silica products of Examples 3A-8A.
Figure 4:
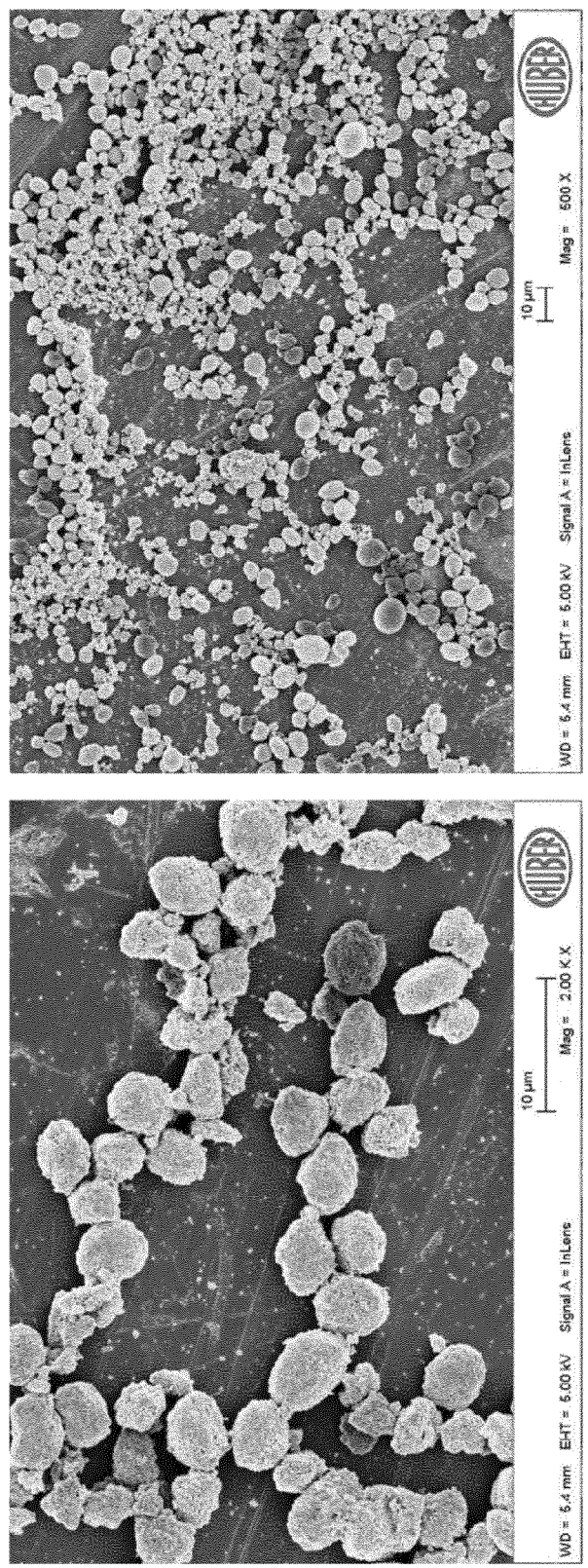
FIG. 4 is Scanning Electron Micrographs of the silica of Example 3A.
Figure 5:
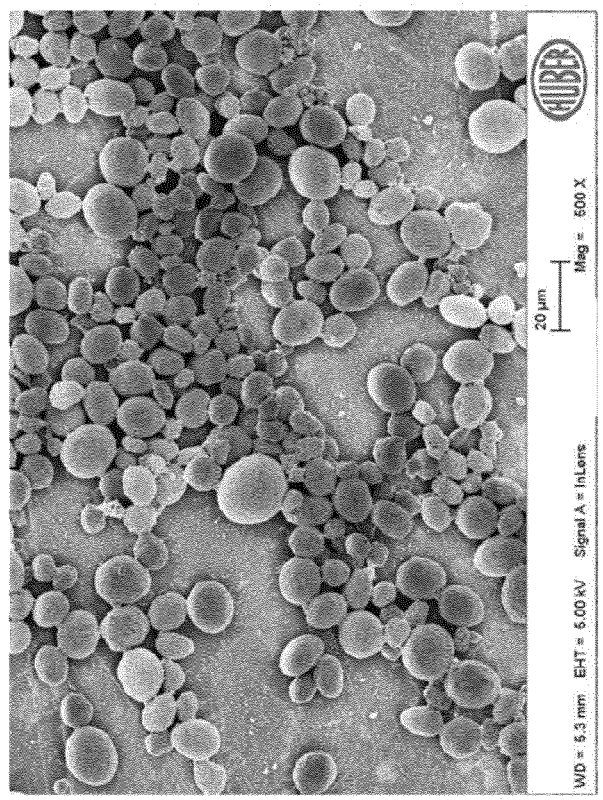
FIG. 5 is Scanning Electron Micrographs of the silica of Example 4A.
Figure 5:
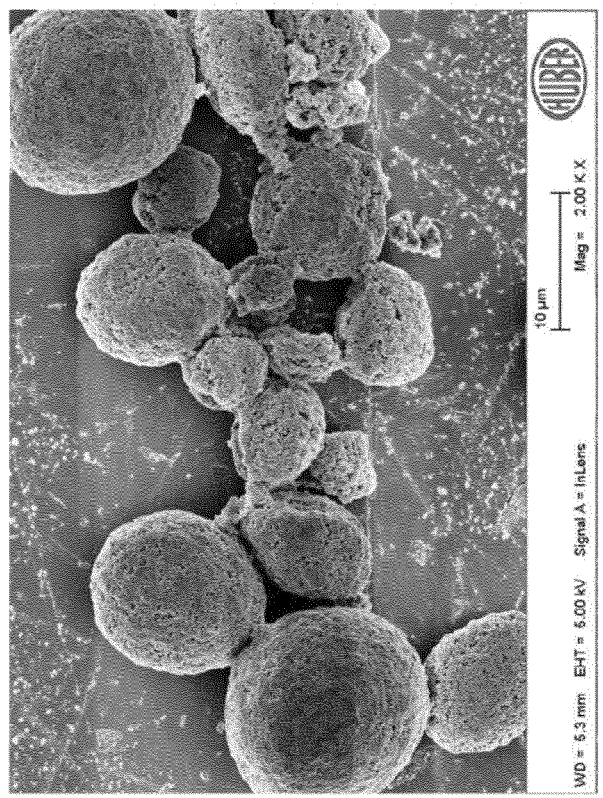
Figure 6:
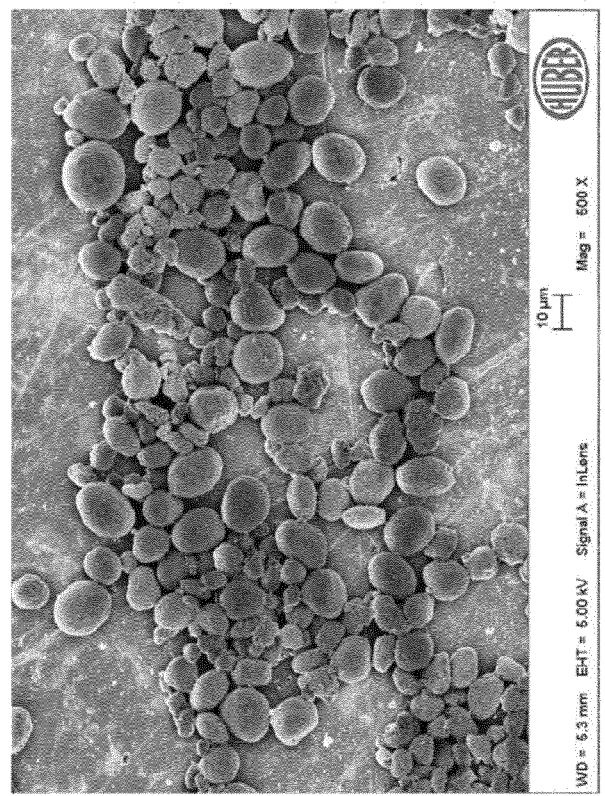
FIG. 6 is Scanning Electron Micrographs of the silica of Example 5A.
Figure 6:
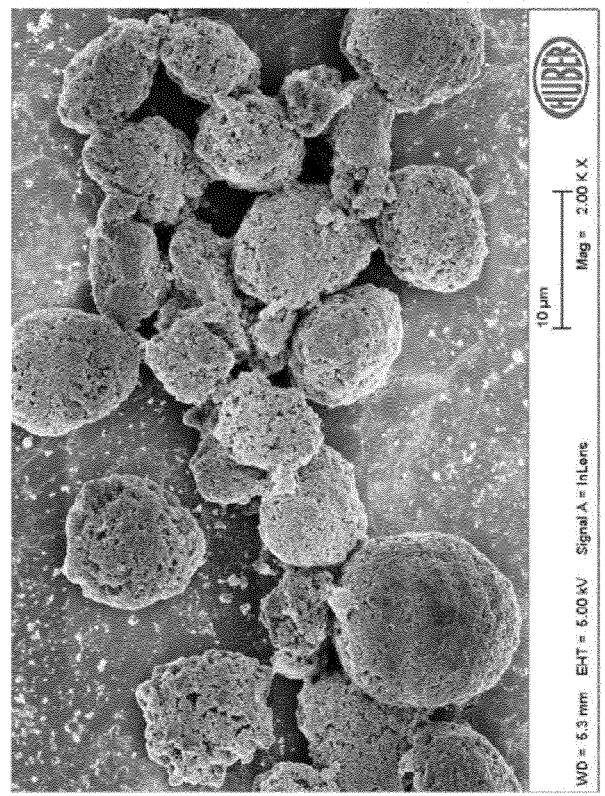
Figure 7:
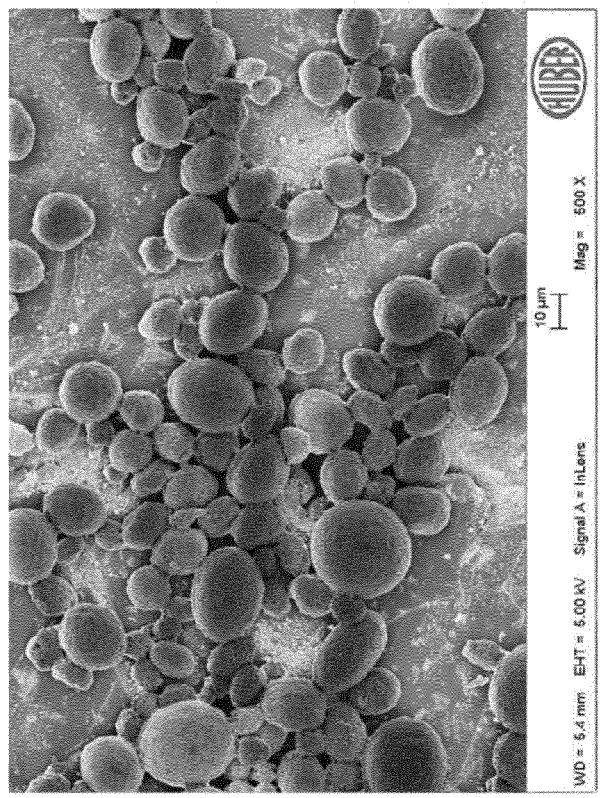
FIG. 7 is Scanning Electron Micrographs of the silica of Example 6A.
Figure 7:
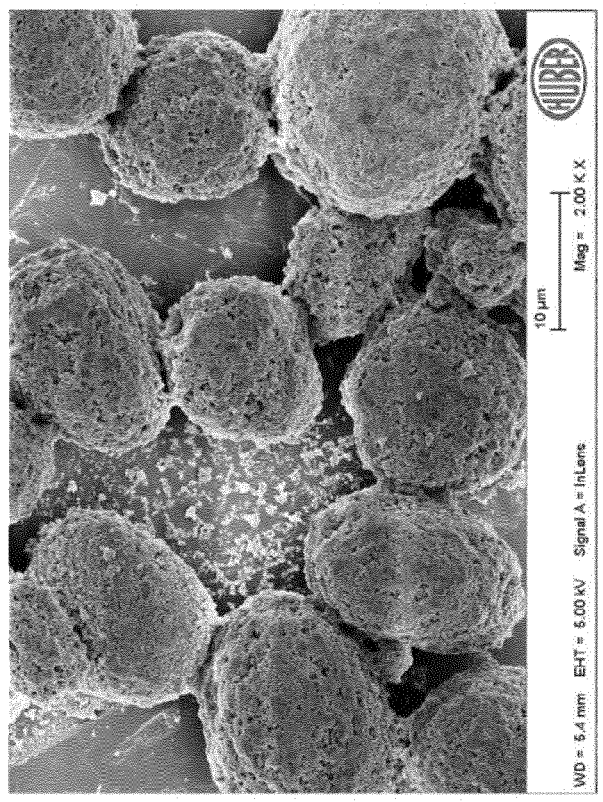
Figure 8:
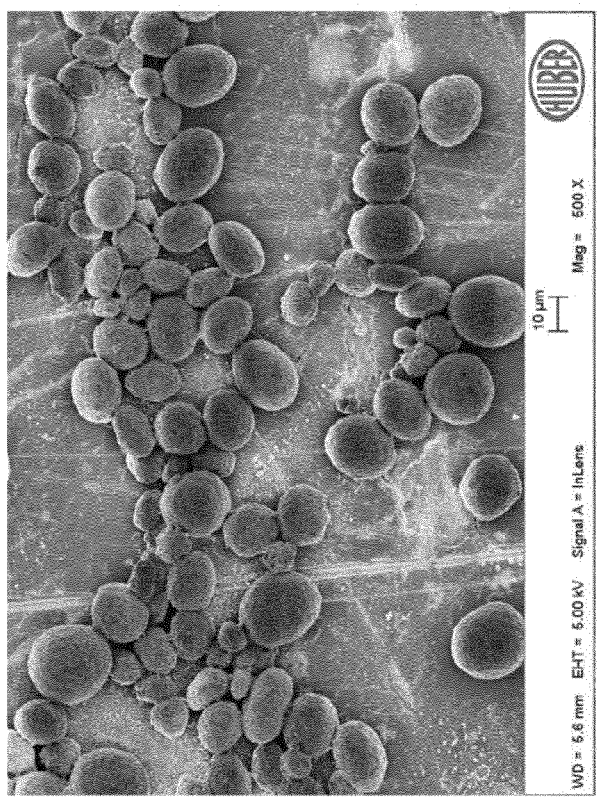
FIG. 8 is Scanning Electron Micrographs of the silica of Example 7A.
Figure 8:
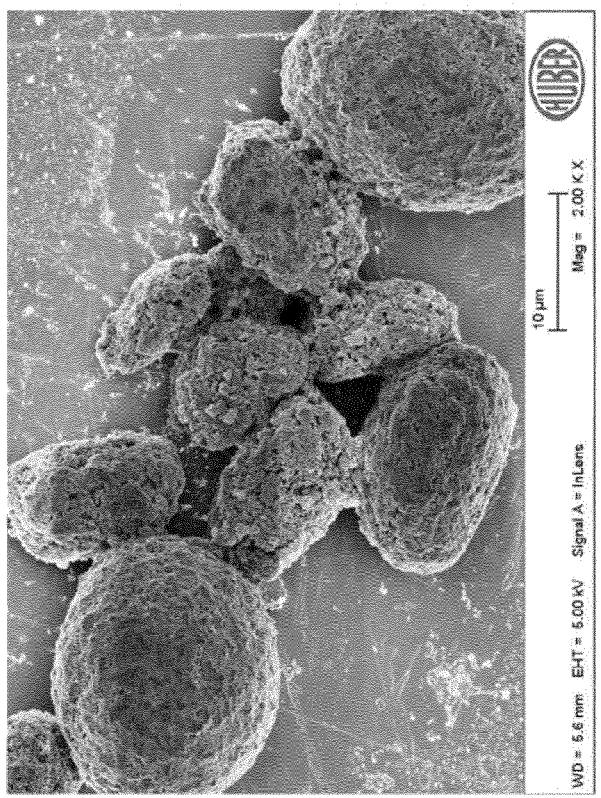
Figure 9:
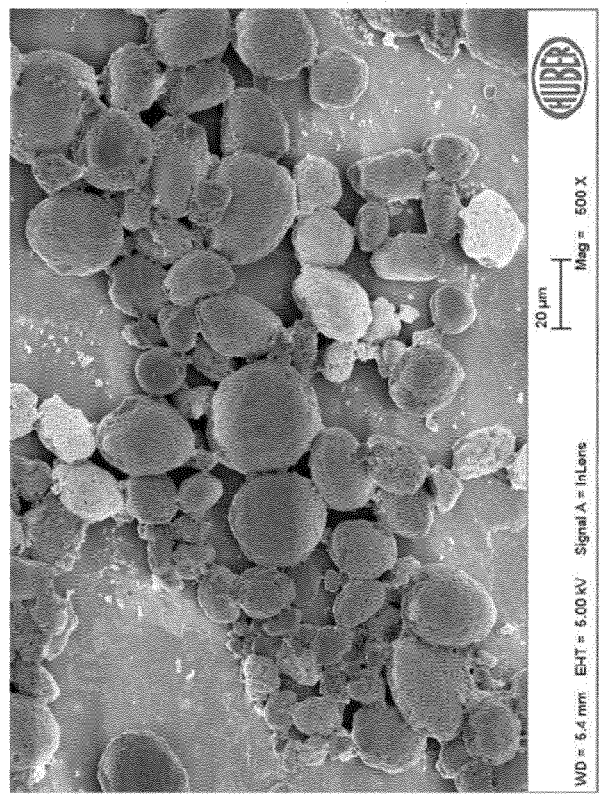
FIG. 9 is Scanning Electron Micrographs of the silica of Example 8A.
Figure 9:
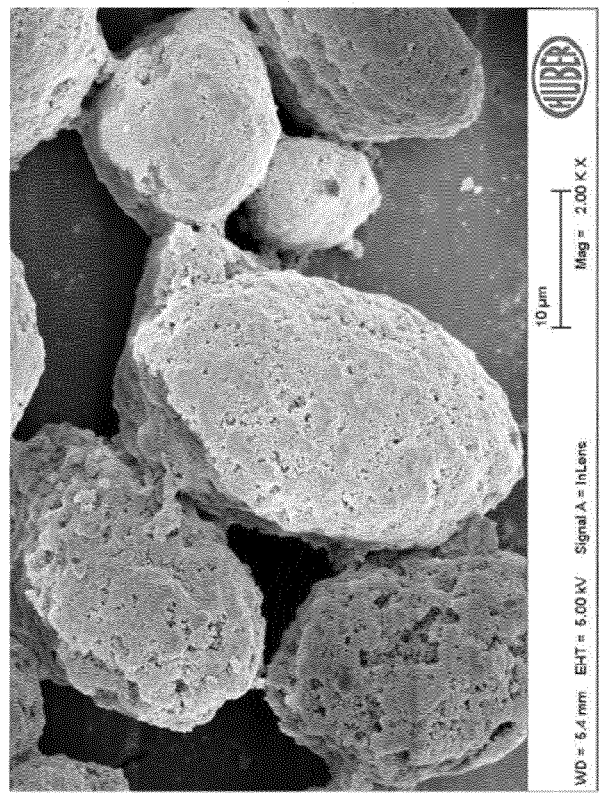

FIG. 3 illustrates the continuous loop reactor apparatus, which was configured in a recycle loop such that reaction slurry was circulated numerous times before it was discharged. The loop was comprised of sections of fixed pipe joined together by sections of flexible hose. The internal diameter of the piping/hose was approximately 1". On one side of the loop, a pump was placed to circulate the reaction slurry, and on the opposite side a Silverson in-line mixer was installed to provide additional shear to the system and also to feed the acid component. In between the pumps, a static mixer heat exchanger was installed to provide a means to control the temperature during production of the silica material. The discharge pipe, located after the acid addition point, allowed the product to discharge as a function of the rates at which silicate and acid were added. The discharge pipe also was fitted with a back pressure valve to enable the system to operate at temperatures greater than 100° C. The product discharge pipe was oriented to collect product into a tank for additional modification (e.g., pH adjustment), or was discharged directly into a rotary or press type filter. Optionally, acid could be added into the product discharge line to avoid pH adjustment when the silica product was prepared at a pH greater than 7.0.

For certain examples, the Silverson in-line mixer was modified to provide a high level of mixing without providing shear. This was accomplished by removing the stator screen from the Silverson mixer and operating the unit with only the backing plate and the normal mixer head. Particle size thus could be controlled by changing the Silverson output rate and the recirculation rate (e.g., a reduction in both rates can increase the average particle size).

Prior to the introduction of acid and silicate into the system for Examples 3A-8A, precipitated silica, sodium sulfate, sodium silicate and water were added and recirculated at 80 L/min. This step was performed to fill the recycle loop with the approximate contents and concentrations of a typical batch to minimize the purging time before the desired product could be collected.

For Example 3A, 1.5 kg of Example 1A, 1.34 kg of sodium sulfate, 11.1 L of sodium silicate (3.32 MR, 19.5%), and 20 L of water were added to the recirculation loop, followed by heating to 95° C. with recirculation at 80 L/min with the Silverson operating at 60 Hz (3485 RPM) with the normal rotor/stator configuration. Sodium silicate (3.32 MR, 20.0%) and sulfuric acid (17.1%) were added simultaneously to the loop at a silicate rate of 1.7 L/min and an acid rate sufficient to maintain a pH of 7.5. If necessary, the acid rate was adjusted accordingly to maintain the pH. Acid and silicate were added under these conditions for 40 minutes to purge unwanted silica out of the system before the desired material was collected. After 40 minutes had passed, the collection vessel was emptied and its contents discarded. The silica product was then collected in a vessel with stirring at 40 RPM while maintaining the temperature at approximately 80° C. After the desired quantity of product was collected, addition of acid and silicate were stopped and the contents of the loop were allowed to circulate. The silica product in the collection vessel was adjusted to pH 6.0 with the manual addition of sulfuric acid and was then filtered, and washed to a conductivity of ~1500 µS. The pH of the slurry was then readjusted to pH 6.0 with sulfuric acid and spray dried.

For Example 4A, 1.5 kg of Example 1A, 1.34 kg of sodium sulfate, 11.1 L of sodium silicate (2.65 MR, 20.0%), and 20 L of water were added to the recirculation loop, followed by heating to 95° C. with recirculation at 80 L/min with the Silverson operating at 60 Hz (3485 RPM) with the stator screen removed. Sodium silicate (2.65 MR, 20.0%) and sulfuric acid (17.1%) were added simultaneously to the loop at a silicate rate of 1.7 L/min and an acid rate sufficient to maintain a pH of 7.5. If necessary, the acid rate was adjusted accordingly to maintain the pH. Acid and silicate were added under these conditions for 40 minutes to purge unwanted silica out of the system before the desired material was collected. After 40 minutes had passed, the collection vessel was emptied and its contents discarded. The silica product was then collected in a vessel with stirring at 40 RPM while maintaining the temperature at approximately 80° C. After the desired quantity of product was collected, addition of acid and silicate were stopped and the contents of the loop were allowed to circulate. The silica product in the collection vessel was adjusted to pH 6.0 with the manual addition of sulfuric acid and was then filtered, and washed to a conductivity of ~1500 µS. The pH of the slurry was then readjusted to pH 6.0 with sulfuric acid and spray dried.

For Example 5A, 1.5 kg of Example 1A, 1.34 kg of sodium sulfate, 11.1 L of sodium silicate (2.65 MR, 26.6%) and 20 L of water were added to the recirculation loop, followed by heating to 95° C. with recirculation at 80 L/min with the Silverson operating at 60 Hz (3485 RPM) with the stator screen removed. Sodium silicate (2.65 MR, 26.6%) and sulfuric acid (22.8%) were added simultaneously to the loop at a silicate rate of 1.7 L/min and an acid rate sufficient to maintain a pH of 7.5. If necessary, the acid rate was adjusted accordingly to maintain the pH. Acid and silicate were added under these conditions for 40 minutes to purge unwanted silica out of the system before the desired material was collected. After 40 minutes had passed, the collection vessel was emptied and its contents discarded. The silica product was then collected in a vessel with stirring at 40 RPM while maintaining the temperature at approximately 80° C. After the desired quantity of product was collected, addition of acid and silicate were stopped and the contents of the loop were allowed to circulate. The silica product in the collection vessel was adjusted to pH 6.0 with the manual addition of sulfuric acid and was then filtered, and washed to a conductivity of ~1500 µS. The pH of the slurry was then readjusted to pH 6.0 with sulfuric acid and spray dried.

For Example 6A, 1.5 kg of Example 1A, 1.34 kg of sodium sulfate, 11.1 L of sodium silicate (2.65 MR, 26.6%) and 20 L of water were added to the recirculation loop, followed by heating to 95° C. with recirculation at 80 L/min with the Silverson operating at 15 Hz (871 RPM) with the stator screen removed. Sodium silicate (2.65 MR, 26.6%) and sulfuric acid (22.8%) were added simultaneously to the loop at a silicate rate of 1.7 L/min and an acid rate sufficient to maintain a pH of 7.5. If necessary, the acid rate was adjusted accordingly to maintain the pH. Acid and silicate were added under these conditions for 40 minutes to purge unwanted silica out of the system before the desired material was collected. After 40 minutes had passed, the collection vessel was emptied and its contents discarded. The silica product was then collected in a vessel with stirring at 40 RPM while maintaining the temperature at approximately 80° C. After the desired quantity of product was collected, addition of acid and silicate were stopped and the contents of the loop were allowed to circulate. The silica product in the collection vessel was adjusted to pH 6.0 with the manual addition of sulfuric acid and was then filtered, and washed to a conductivity of ~1500 µS. The pH of the slurry was then readjusted to pH 6.0 with sulfuric acid and spray dried.

For Example 7A, 1.5 kg of Example 1A, 1.34 kg of sodium sulfate, 11.1 L of sodium silicate (2.65 MR, 26.6%) and 20 L of water were added to the recirculation loop, followed by heating to 95° C. with recirculation at 80 L/min with the Silverson operating at 30 Hz (1743 RPM) with the stator screen removed. Sodium silicate (2.65 MR, 26.6%) and sulfuric acid (22.8%) were added simultaneously to the loop at a silicate rate of 1.7 L/min and an acid rate sufficient to maintain a pH of 7.5. If necessary, the acid rate was adjusted accordingly to maintain the pH. Acid and silicate were added under these conditions for 40 minutes to purge unwanted silica out of the system before the desired material was collected. After 40 minutes had passed, the collection vessel was emptied and its contents discarded. The silica product was then collected in a vessel with stirring at 40 RPM while maintaining the temperature at approximately 80° C. After the desired quantity of product was collected, addition of acid and silicate were stopped and the contents of the loop were allowed to circulate. The silica product in the collection vessel was adjusted to pH 6.0 with the manual addition of sulfuric acid and was then filtered, and washed to a conductivity of ~1500 µS. The pH of the slurry was then readjusted to pH 6.0 with sulfuric acid and spray dried.

For Example 8A, 1.5 kg of Example 1A, 1.34 kg of sodium sulfate, 11.1 L of sodium silicate (3.32 MR, 32.3%) and 20 L of water were added to the recirculation loop, followed by heating to 90° C. with recirculation at 80 L/min with the Silverson operating at 30 Hz (1742 RPM) with the stator screen removed. Sodium silicate (3.32 MR, 32.2%) and sulfuric acid (22.8%) were added simultaneously to the loop at a silicate rate of 1.7 L/min and an acid rate sufficient to maintain a pH of 7.5. If necessary, the acid rate was adjusted accordingly to maintain the pH. Acid and silicate were added under these conditions for 40 minutes to purge unwanted silica out of the system before the desired material was collected. After 40 minutes had passed, the collection vessel was emptied and its contents discarded. The silica product was then collected in a vessel with stirring at 40 RPM while maintaining the temperature at approximately 80° C. After the desired quantity of product was collected, addition of acid and silicate were stopped and the contents of the loop were allowed to circulate. The silica product in the collection vessel was adjusted to pH 6.0 with the manual addition of sulfuric acid and was then filtered, and washed to a conductivity of ~1500 µS. The pH of the slurry was then readjusted to pH 6.0 with sulfuric acid and spray dried.

Table I summarizes certain properties of the silica particles produced in Examples 3A-8A, as compared to the respective properties of Comparative Examples 1A-2A. Examples 3A-8A encompassed a wide median (d50) particle size range of approximately 3 to 21 µm, but with narrow particle size distributions. Examination of SEM images also demonstrated a narrow particle size distribution and spherical particle morphology. Representative SEM images for Examples 3A-8A are provided as FIGS. 4-9, respectively. The respective sphericity factor ($S_{80}$) for each of Examples 3A-8A was greater than 0.9.

Examples 1B-8B

Examples 3C & 7C

Toothpaste Formulations and PCR and RDA Testing

Samples of silicas 1A-8A were used in toothpaste formulations 1B-8B at a 20 wt. % loading of the respective silica, and in toothpaste formulations 3C and 7C at a 10 wt. % loading of the respective silica, as summarized in Table II.

PCR and RDA testing (at the Indiana University School of Dentistry) were conducted on the toothpaste formulations to determine the impact of the silica properties on the PCR and RDA performance. Table III summarizes the PCR and RDA data for the toothpaste formulations. Unexpectedly, as the particle size of the highly spherical particles increased, the RDA decreased significantly, and to a lesser extent, the PCR also decreased. These results are unexpected and contrary to that typically observed with traditional precipitated silica materials (which are irregularly shaped, and not spherical). While not wishing to be bound by theory, it is believed that since RDA testing is performed on an irregular surface comprised of dentin and hollow dentin tubules that are approximately 2-3 µm in size, that the spherical silica particles fall partway into the tubules, and then gouge the opposite wall as they are pushed out of the tubule by the toothbrush as they move across the dentin surface.

Examples 9A-13A

Irregular Silica Particles

Table IV summarizes certain properties of comparative silica materials 9A-13A, which have an irregular and non-spherical particle morphology. Example 9A was a conventional silica material commercially available from Huber Engineered Materials, and Examples 10A-13A were produced by air milling an unmilled sample of Example 9A to a d50 particle size of 3.5 µm (Example 10A), 6.2 µm (Example 11A), 9.4 µm (Example 12A, broad particle size distribution), and 9.3 µm (Example 13A, narrow particle size distribution).

Examples 9B-13B

Toothpaste Formulations and PCR and RDA Testing

Samples of silicas 9A-13A were used in toothpaste formulations 9B-13B at a 20 wt. % loading of the respective silica, as summarized in Table V.

PCR and RDA testing (at the Indiana University School of Dentistry) were conducted on the toothpaste formulations to determine the impact of the silica properties on the PCR and RDA performance. Table VI summarizes the PCR and RDA data for the toothpaste formulations. As shown in Table VI, as the particle size of the silica increased from 3.5 µm to 9.5 µm, there was no change in either the RDA or the PCR values. Thus, for irregular and non-spherical silica particles, there is no correlation between particle size and RDA and no correlation between particle size and PCR.

Discussion of Examples

By comparing the data in Table III with that of Table VI, the behavior of the spherical silica materials is fundamentally (and surprisingly) different from that of traditional dental silicas, which are non-spherical and irregularly shaped. Particle size and particle size distribution can be used to control RDA and PCR with highly spherical materials, whereas for traditional irregularly-shaped silicas, particle size and particle size distribution have no significant effect.

While not wishing to be bound by the following theory, it is believed that the spherical particles initially gouge into the substrate, before they begin rolling across the surface (initially there is a lot of wear, but as the particles begin to roll, the wear is essentially eliminated), whereas a traditional non-spherical and irregularly shaped product would scratch the entire way across the substrate.

Figure 10:
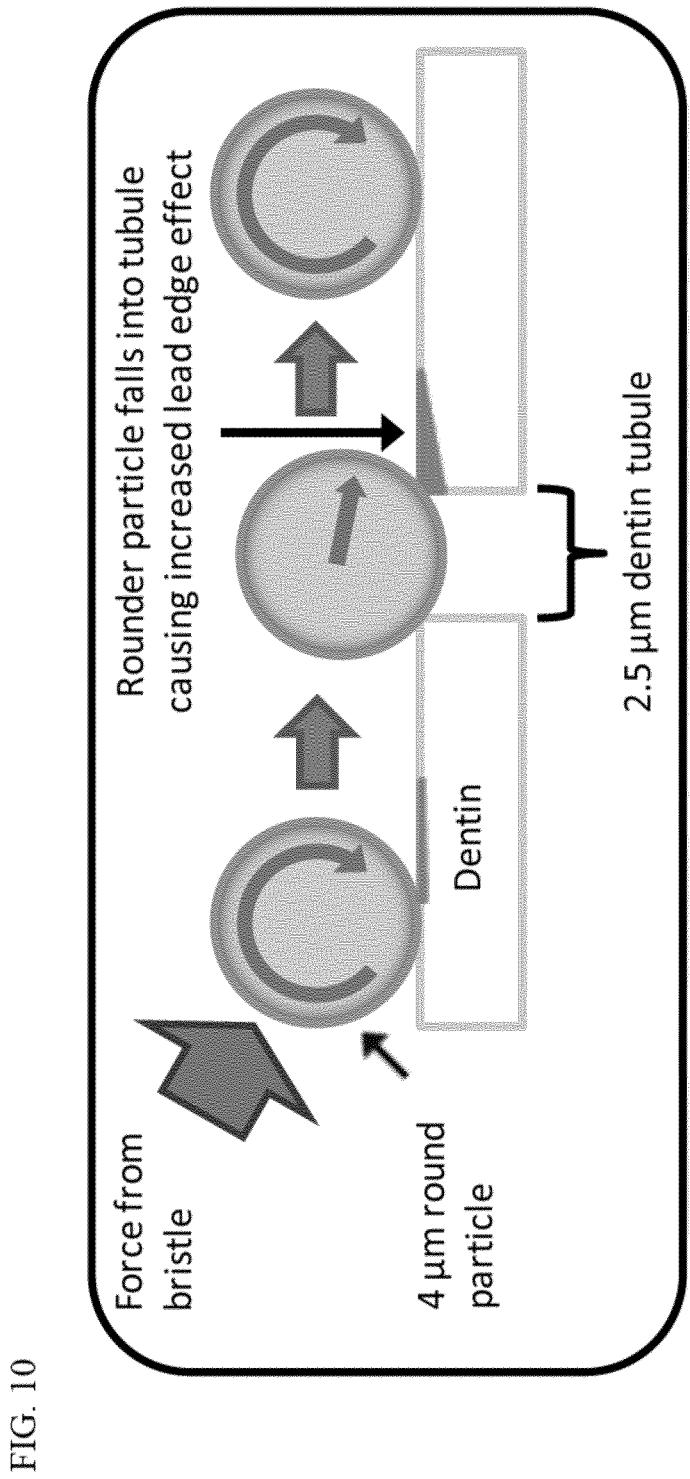
FIG. 10 is a model for a 4 µm spherical particle interacting with a 2.5 µm dentin tubule.

As shown in Table III, the RDA values for spherical products with small particle sizes (less than 4 µm) are greater than 200. It is postulated that since the dentin surface is essentially non-homogeneous, comprised of both porous mineral and organic content, the spherical particles partially enter tubules and scrape the opposite side as they exit. With very spherical particles, as the particle size is increased, the depth that they can enter a tubule is reduced. This reduction in penetration in the tubule (and increase in particle size) is thought to be the driving factor for reducing RDA. A model for the spherical particle (at a small particle size) interacting with a dentin tubule is illustrated in FIG. 10.

Figure 11:
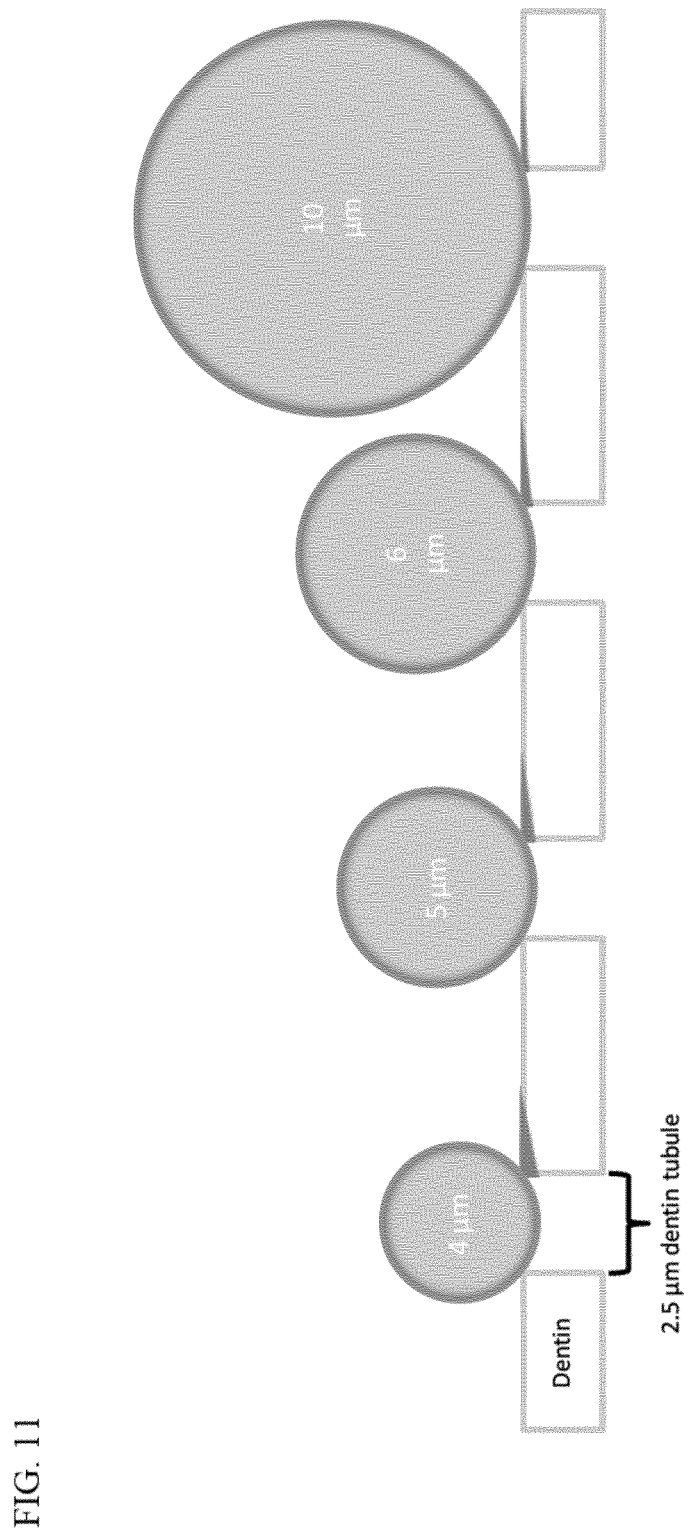
FIG. 11 is a model for a spherical particles of increasing particle size (4 µm, 5 µm, 6 µm, 10 µm) interacting with dentin tubules of 2.5 µm.

A simple analogy would be driving over a pothole with a car tire. If the pothole is large relative to the car tire, a large bump is felt as the car passes over the pothole. As the pothole is decreased in size, the intensity of the bump that is felt decreases, until the pothole is small enough that the car tire does not fall very far into the hole. If the pothole was a fixed size, the same effect would be observed as the tires on the car were increased in size. In like manner, a model of spherical particles of increasing particle size (4 µm, 5 µm, 6 µm, 10 µm) interacting with dentin tubules of approximately 2.5 µm in size in shown in FIG. 11. The penetration depth of the particles into the tubules is reduced as particle size increases.

Figure 12:
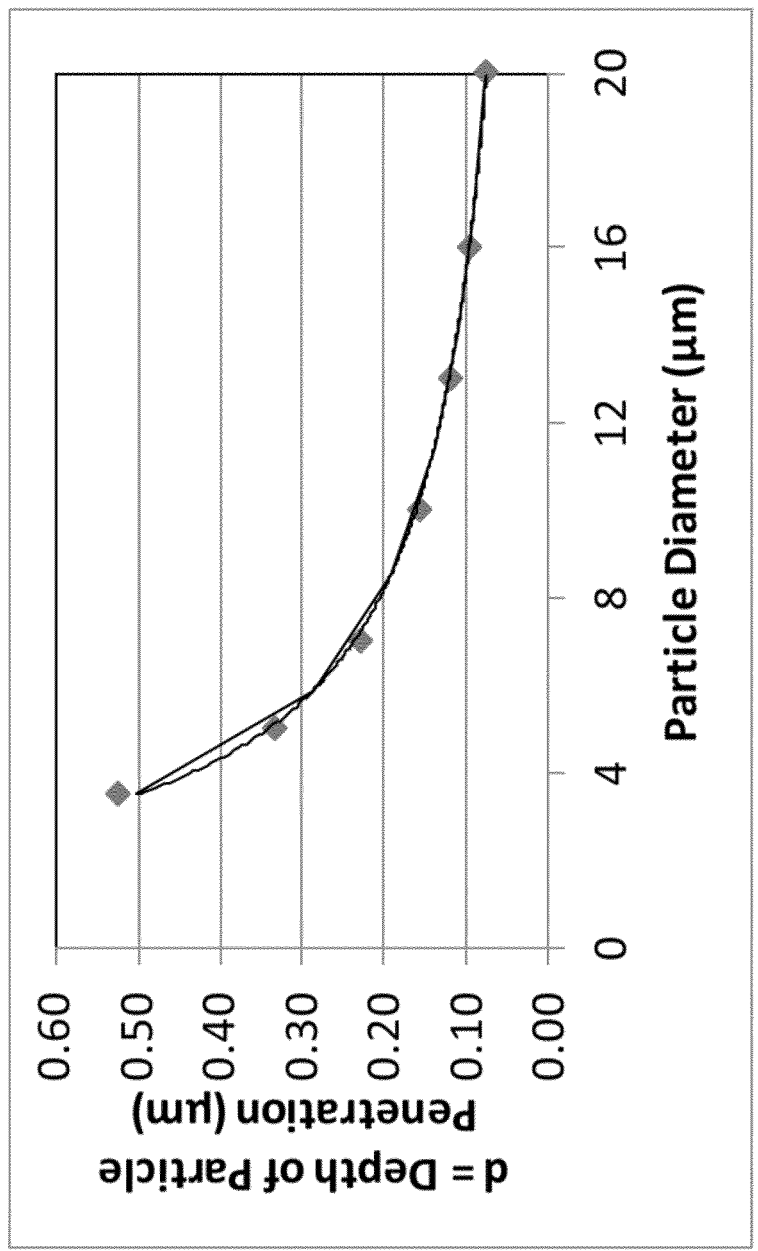
FIG. 12 is a plot of the depth of penetration, in a 2.5 µm width dentin tubule, versus particle diameter for a sphere.

Using geometric calculations, the depth of penetration for a spherical particle can be calculated based upon its diameter, as described by J. M. Fildes et al., Wear 274-275 (2012) 414-422, incorporated herein by reference in its entirety. As it pertains to silica particle sizes and the 2.5 μm width dentin tubules relevant to RDA, a plot of the depth of penetration versus particle diameter for a sphere can be generated (see FIG. 12). There is a reduction in the depth of penetration of highly spherical particles of roughly 80% as the particle size increases from 3.5 μm to 12 μm.

Figure 13:
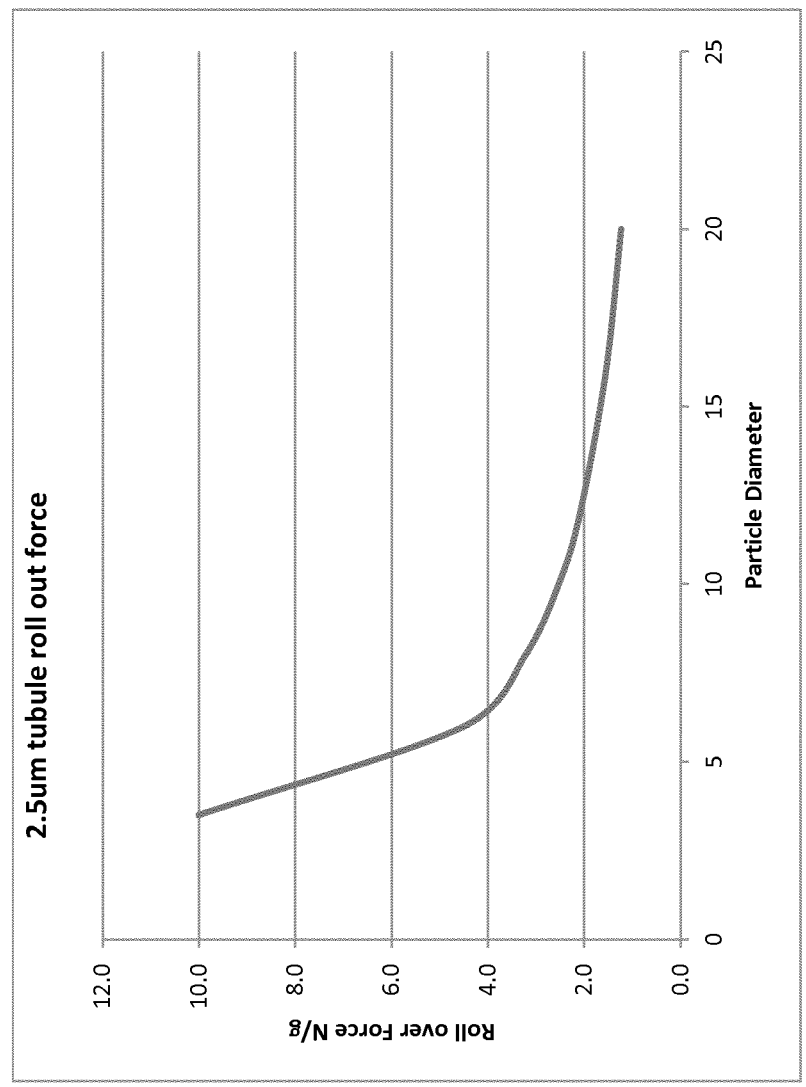
FIG. 13 is a plot of the force required to roll a sphere out of a 2.5 µm width tubule as a function of increasing particle diameter for a sphere.

The force required for a circular wheel (analogous to a spherical particle) to pass over a step of different heights (analogous to a depth of penetration) also can be calculated using formulas in "Physics for Scientists and Engineers" Eighth Edition (2010); Serway|Jewett, incorporated herein by reference in its entirety. Using the assumption that the spherical particle only contacts one part of the tubule as it passes through (with the exception of when it is at the bottom, then the point of contact is a step), a rough estimate of the force required for the particle to exit the tubule can be calculated. Because dentifrice compositions are loaded by weight and numerically there are more small particles than large particles, it is believed that the calculated force in Newtons should be on a weight basis (per gram basis). FIG. 13 graphically represents the decrease in force required for 1 gram of spherical particles to exit a 2.5 μm tubule as a function of increasing particle size. The force is reduced by over 50% as the particle size increases from 6 μm to 12 μm.

In sum, the figures, tables, and discussion above demonstrate that the behavior of the spherical silica materials is fundamentally (and unexpectedly) different from that of traditional dental silicas, which are non-spherical and irregularly shaped, particularly as it pertains to RDA performance. Particle size is a key factor to control RDA and PCR with highly spherical materials, unlike traditional irregularly-shaped silicas, where particle size has no significant effect.

TABLE I

Examples 1A-8A.

| | Example | | | | | | | |
|---|---|---|---|---|---|---|---|---|
| | 1A | 2A | 3A | 4A | 5A | 6A | 7A | 8A |
| Description | Irregular Silica | Irregular Silica | Spherical Silica | Spherical Silica | Spherical Silica | Spherical Silica | Spherical Silica | Spherical Silica |
| Einlehner (mg lost/100k rev) | 15.2 | 3.7 | 3.1 | 3.3 | 2.5 | 2.9 | 3.1 | 0.9 |
| BET Surface Area (m$^2$/g) | 56 | 85 | 89 | 59 | 66 | 64 | 48 | 157 |
| CTAB Surface Area (m$^2$/g) | 63 | 66 | 56 | 29 | 20 | 29 | 26 | 93 |
| Oil Absorption (cc/100 g) | 53 | 81 | 66 | 38 | 39 | 40 | 40 | 70 |
| Water AbC (cc/100 g) | 70 | 108 | 75 | 67 | 69 | 68 | 63 | 99 |
| 5% pH | 7.4 | 7.3 | 7.2 | 6.8 | 6.8 | 7.0 | 7.3 | 7.1 |
| Moisture (%) | 6.5 | 6.8 | 3.2 | 2.8 | 2.2 | 2.6 | 1.8 | 3.6 |
| Median Particle Size (μm) | 9.7 | 9.1 | 3.5 | 8.8 | 10.7 | 13.0 | 14.0 | 20.8 |
| Mean Particle Size (μm) | 12.5 | 11.2 | 3.8 | 8.7 | 10.6 | 12.9 | 13.9 | 20.9 |
| Ratio of (d90-d10)/d50 | 3.2 | 2.9 | 1.4 | 1.6 | 1.7 | 1.7 | 1.7 | 1.7 |
| 325 Mesh Residue (wt. %) | 1.12 | 0.70 | 0.01 | 0.20 | 0.10 | 0.20 | 0.10 | 1.00 |
| Sodium Sulfate (%) | 2.08 | 1.14 | 0.82 | 0.59 | 0.66 | 0.35 | 2.24 | 0.35 |
| Pour Density (lb/ft$^3$) | 26.0 | 18.0 | 30.2 | 34.7 | 37.5 | 39.0 | 42.6 | 33.4 |
| Pack Density (lb/ft$^3$) | 45.0 | 28.0 | 46.8 | 52.0 | 55.1 | 52.0 | 55.1 | 42.6 |

TABLE II

Examples 1B-8B and Examples 3C and 7C-Toothpaste formulations used for PCR/RDA testing (all values in wt. %)

| | Example | | | | | | | | | |
|---|---|---|---|---|---|---|---|---|---|---|
| | 1B | 2B | 3B | 3C | 4B | 5B | 6B | 7B | 7C | 8B |
| Glycerin (99.7%) | 11.000 | 11.000 | 11.000 | 11.000 | 11.000 | 11.000 | 11.000 | 11.000 | 11.000 | 11.000 |
| Sorbitol (70.0%) | 40.007 | 40.007 | 40.007 | 40.007 | 40.007 | 40.007 | 40.007 | 40.007 | 40.007 | 40.007 |
| Deionized water | QS | QS | QS | QS | QS | QS | QS | QS | QS | QS |
| PEG-12 | 3.000 | 3.000 | 3.000 | 3.000 | 3.000 | 3.000 | 3.000 | 3.000 | 3.000 | 3.000 |
| Cekol 2000A | 1.200 | 1.200 | 1.200 | 1.200 | 1.200 | 1.200 | 1.200 | 1.200 | 1.200 | 1.200 |
| Tetrasodium pyrophosphate | 0.500 | 0.500 | 0.500 | 0.500 | 0.500 | 0.500 | 0.500 | 0.500 | 0.500 | 0.500 |
| Sodium saccharin | 0.200 | 0.200 | 0.200 | 0.200 | 0.200 | 0.200 | 0.200 | 0.200 | 0.200 | 0.200 |
| Sodium fluoride | 0.243 | 0.243 | 0.243 | 0.243 | 0.243 | 0.243 | 0.243 | 0.243 | 0.243 | 0.243 |
| Zeoden 165 Silica | 1.500 | 1.500 | 1.500 | 5.000 | 1.500 | 1.500 | 1.500 | 1.500 | 5.000 | 1.500 |
| Example 1A | 20 | | | | | | | | | |
| Example 2A | | 20 | | | | | | | | |
| Example 3A | | | 20 | | | | | | | |
| Example 3A | | | | 10 | | | | | | |
| Example 4A | | | | | 20 | | | | | |
| Example 5A | | | | | | 20 | | | | |
| Example 6A | | | | | | | 20 | | | |
| Example 7A | | | | | | | | 20 | | |
| Example 7A | | | | | | | | | 10 | |
| Example 8A | | | | | | | | | | 20 |

TABLE II-continued

Examples 1B-8B and Examples 3C and 7C-Toothpaste formulations used for PCR/RDA testing (all values in wt. %)

| | Example | | | | | | | | | |
|---|---|---|---|---|---|---|---|---|---|---|
| | 1B | 2B | 3B | 3C | 4B | 5B | 6B | 7B | 7C | 8B |
| Titanium dioxide | 0.500 | 0.500 | 0.500 | 0.500 | 0.500 | 0.500 | 0.500 | 0.500 | 0.500 | 0.500 |
| Sodium lauryl sulfate | 1.200 | 1.200 | 1.200 | 1.200 | 1.200 | 1.200 | 1.200 | 1.200 | 1.200 | 1.200 |
| Flavor | 0.650 | 0.650 | 0.650 | 0.650 | 0.650 | 0.650 | 0.650 | 0.650 | 0.650 | 0.650 |
| Total | 100 | 100 | 100 | 100 | 100 | 100 | 100 | 100 | 100 | 100 |

TABLE III

Examples 1B-8B and Examples 3C and 7C-PCR and RDA data

| | Example | | | | | | | | | |
|---|---|---|---|---|---|---|---|---|---|---|
| | 1B | 2B | 3B | 3C | 4B | 5B | 6B | 7B | 7C | 8B |
| Median Particle Size (μm) | 9.7 | 9.1 | 3.5 | 3.5 | 8.8 | 10.7 | 13.0 | 14.0 | 14.0 | 20.8 |
| Mean Particle Size (μm) | 12.5 | 11.2 | 3.8 | 3.8 | 8.7 | 10.6 | 12.9 | 13.9 | 13.9 | 20.9 |
| Example Silica (wt. %) | 20 | 20 | 20 | 10 | 20 | 20 | 20 | 20 | 10 | 20 |
| PCR | 106 | 82 | 118 | 104 | 93 | 89 | 86 | 85 | 70 | 68 |
| RDA | 180 | 105 | 270 | 245 | 160 | 145 | 127 | 128 | 107 | 55 |

TABLE IV

Examples 9A-13A.

| Example | 9A | 10A | 11A | 12A | 13A |
|---|---|---|---|---|---|
| Einlehner (mg lost/100k rev) | 15.2 | 11.0 | 15.8 | 16.5 | 16.4 |
| BET Surface Area (m²/g) | 56 | 47 | 44 | 45 | 50 |
| CTAB Surface Area (m²/g) | 63 | 40 | 36 | 38 | 26 |
| Oil Absorption (cm³/100 g) | 53 | 62 | 50 | 53 | 58 |
| Water AbC (cm³/100 g) | 70 | 75 | 68 | 68 | 71 |
| 5% pH | 7.4 | 7.8 | 7.8 | 7.7 | 7.8 |
| Moisture (%) | 6.5 | 6.4 | 10.4 | 10.2 | 5.6 |
| Median Particle Size (μm) | 9.7 | 3.5 | 6.2 | 9.4 | 9.3 |
| Mean Particle Size (μm) | 12.5 | 3.8 | 7.6 | 12.5 | 10.1 |
| Ratio of (d90-d10)/d50 | 3.2 | — | — | — | — |
| 325 Mesh Residue (wt. %) | 1.12 | 0.20 | 1.5 | 3.8 | 0.4 |
| Sodium Sulfate (%) | 2.08 | 1.14 | 1.14 | 1.14 | 1.00 |
| Pour Density (lb/ft³) | 26.0 | 17.0 | 22.0 | 26.0 | 26.0 |
| Pack Density (lb/ft³) | 45.0 | 25.0 | 39.0 | 39.0 | 45.0 |

TABLE V

Examples 9B-13B-Toothpaste formulations used for PCR/RDA testing (all values in wt. %)

| Example | 9B | 10B | 11B | 12B | 13B |
|---|---|---|---|---|---|
| Glycerin (99.7%) | 11.000 | 11.000 | 11.000 | 11.000 | 11.000 |
| Sorbitol (70.0%) | 40.007 | 40.007 | 40.007 | 40.007 | 40.007 |
| Deionized water | QS | QS | QS | QS | QS |
| PEG-12 | 3.000 | 3.000 | 3.000 | 3.000 | 3.000 |
| Cekol 2000A | 1.200 | 1.200 | 1.200 | 1.200 | 1.200 |
| Tetrasodium pyrophosphate | 0.500 | 0.500 | 0.500 | 0.500 | 0.500 |
| Sodium saccharin | 0.200 | 0.200 | 0.200 | 0.200 | 0.200 |
| Sodium fluoride | 0.243 | 0.243 | 0.243 | 0.243 | 0.243 |
| Zeodent 165 Silica | 1.500 | 1.500 | 1.500 | 1.500 | 1.500 |
| Example 9A | 20 | | | | |
| Example 10A | | 20 | | | |
| Example 11A | | | 20 | | |
| Example 12A | | | | 20 | |
| Example 13A | | | | | 20 |
| Titanium dioxide | 0.500 | 0.500 | 0.500 | 0.500 | 0.500 |
| Sodium lauryl sulfate | 1.200 | 1.200 | 1.200 | 1.200 | 1.200 |
| Flavor | 0.650 | 0.650 | 0.650 | 0.650 | 0.650 |
| Total | 100 | 100 | 100 | 100 | 100 |

TABLE VI

Examples 9B-13B-PCR and RDA data

| Example | 9B | 10B | 11B | 12B | 13B |
|---|---|---|---|---|---|
| Median Particle Size (μm) | 9.7 | 3.5 | 6.2 | 9.4 | 9.3 |
| Mean Particle Size (μm) | 12.5 | 3.8 | 7.6 | 12.5 | 10.1 |
| Example Silica (wt. %) | 20 | 20 | 20 | 20 | 20 |
| PCR (IU) | 102 | 108 | 103 | 105 | 106 |
| RDA (IU) | 212 | 218 | 216 | 222 | 214 |

The invention is described above with reference to numerous aspects and specific examples. Many variations will suggest themselves to those skilled in the art in light of the above detailed description. All such obvious variations are within the full intended scope of the appended claims. Other aspects of the invention can include, but are not limited to, the following (aspects are described as "comprising" but, alternatively, can "consist essentially of" or "consist of"):

Aspect 1. Silica particles characterized by:
(i) a d50 median particle size of greater than or equal to about 6 μm;
(ii) a ratio of (d90−d10)/d50 in a range from about 1.1 to about 2.4;
(iii) a RDA at 20 wt. % loading in a range from about 40 to about 200; and
(iv) a sphericity factor ($S_{80}$) of greater than or equal to about 0.9.

Aspect 2. The silica particles of Aspect 1, wherein the d50 median particle size is in a range from about 7 to about 25 μm.

Aspect 3. The silica particles of Aspect 1, wherein the d50 median particle size is in a range from about 8 to about 20 μm.

Aspect 4. The silica particles of any one of Aspects 1-3, wherein the ratio of (d90−d10)/d50 is in a range from about 1.1 to about 2.2.

Aspect 5. The silica particles of any one of Aspects 1-3, wherein the ratio of (d90−d10)/d50 is in a range from about 1.2 to about 2.

Aspect 6. The silica particles of any one of Aspects 1-5, wherein the RDA at 20 wt. % loading is in a range from about 50 to about 190.

Aspect 7. The silica particles of any one of Aspects 1-5, wherein the RDA at 20 wt. % loading is in a range from about 85 to about 180.

Aspect 8. The silica particles of any one of Aspects 1-7, wherein the silica particles are further characterized by an oil absorption in a range from about 30 to about 115 cc/100 g.

Aspect 9. The silica particles of any one of Aspects 1-7, wherein the silica particles are further characterized by an oil absorption in a range from about 30 to about 90 cc/100 g.

Aspect 10. The silica particles of any one of Aspects 1-9, wherein the silica particles are further characterized by a pack density in a range from about 25 to about 65 lb/ft³.

Aspect 11. The silica particles of any one of Aspects 1-9, wherein the silica particles are further characterized by a pack density in a range from about 40 to about 60 lb/ft³.

Aspect 12. The silica particles of any one of Aspects 1-11, wherein the silica particles are further characterized by a BET surface area in a range from about 10 to about 200 m²/g.

Aspect 13. The silica particles of any one of Aspects 1-11, wherein the silica particles are further characterized by a BET surface area in a range from about 20 to about 100 m²/g.

Aspect 14. The silica particles of any one of claims 1-13, wherein the silica particles are further characterized by a 325 mesh residue of less than or equal to about 1.2 wt. %.

Aspect 15. The silica particles of any one of Aspects 1-13, wherein the silica particles are further characterized by a 325 mesh residue of less than or equal to about 0.5 wt. %.

Aspect 16. The silica particles of any one of Aspects 1-15, wherein the sphericity factor ($S_{80}$) is greater than or equal to about 0.92.

Aspect 17. The silica particles of any one of Aspects 1-15, wherein the sphericity factor ($S_{80}$) is greater than or equal to about 0.94.

Aspect 18. The silica particles of any one of Aspects 1-17, wherein the silica particles are further characterized by an Einlehner abrasion value in a range from about 0.5 to about 7 mg lost/100,000 revolutions.

Aspect 19. The silica particles of any one of Aspects 1-18, wherein the silica particles are precipitated silica particles.

Aspect 20. The silica particles of any one of Aspects 1-19, wherein the silica particles are amorphous.

Aspect 21. A composition comprising the silica particles of any one of Aspects 1-20.

Aspect 22. A dentifrice composition comprising the silica particles of any one of Aspects 1-20.

Aspect 23. A dentifrice composition comprising from about 0.5 to about 50 wt. % of the silica particles of any one of Aspects 1-20.

Aspect 24. A dentifrice composition comprising from about 5 to about 35 wt. % of the silica particles of any one of Aspects 1-20.

Aspect 25. The dentifrice composition of any one of Aspects 22-24, wherein the composition further comprises at least one of a humectant, a solvent, a binder, a therapeutic agent, a chelating agent, a thickener other than the silica particles, a surfactant, an abrasive other than the silica particles, a sweetening agent, a colorant, a flavoring agent, and a preservative, or any combination thereof.

Aspect 26. A process for producing silica particles, the process comprising:
(a) continuously feeding a mineral acid and an alkali metal silicate into a loop reaction zone comprising a stream of liquid medium, wherein at least a portion of the mineral acid and the alkali metal silicate react to form the silica particles in the liquid medium of the loop reaction zone;
(b) continuously recirculating the liquid medium through the loop reaction zone, wherein the loop reaction zone does not comprise a stator screen or the loop reaction zone comprises a stator screen with openings greater than 3 mm² in cross sectional area, or a shear frequency in the loop reaction zone is less than 1,000,000 interactions/min, or both; and
(c) continuously discharging from the loop reaction zone a portion of the liquid medium comprising the silica particles.

Aspect 27. The process of Aspect 26, wherein steps (a)-(c) are performed simultaneously.

Aspect 28. The process of Aspect 26 or 27, wherein the loop reaction zone comprises a continuous loop of one or more loop reactor pipes.

Aspect 29. The process of any one of Aspects 26-28, wherein:
the mineral acid and the alkali metal silicate are fed into the loop reaction zone at different points along the loop reaction zone;
the mineral acid comprises sulfuric acid, hydrochloric acid, nitric acid, phosphoric acid, or a combination thereof; and the alkali metal silicate comprises sodium silicate.

Aspect 30. The process of any one of Aspects 26-29, wherein the liquid medium is recirculated through the loop reaction zone at a pH in a range from about 6 to about 10.

Aspect 31. The process of any one of Aspects 26-30, wherein:

the portion of the liquid medium discharged from the loop reaction zone is discharged in a volumetric rate proportional to the amount of the mineral acid and the alkali metal silicate fed into the loop reaction zone; and steps (a)-(c) are performed in a continuous single loop reactor.

Aspect 32. The process of any one of Aspects 26-31, wherein the liquid medium is recirculated through the loop reaction zone at a rate in a range from about 15 L/min to about 150 L/min.

Aspect 33. The process of any one of Aspects 26-32, wherein the liquid medium is recirculated through the loop reaction zone at a rate ranging from about 50 vol. % per minute to about 1000 vol. % per minute.

Aspect 34. The process of any one of Aspects 26-33, wherein all or greater than 95 wt. % of the liquid medium is recirculated in step (b).

Aspect 35. The process of any one of Aspects 26-34, wherein step (b) is conducted at a temperature in a range about 85 to about 100° C.

Aspect 36. The process of any one of Aspects 26-35, further comprising a step of pH adjusting after step (c), a step of filtering after step (c), a step of washing after step (c), a step of drying after step (c), or any combination thereof.

Aspect 37. The process of any one of Aspects 26-36, wherein the silica particles are characterized by:

(i) a d50 median particle size of greater than or equal to about 6 μm;

(ii) a ratio of (d90−d10)/d50 in a range from about 1.1 to about 2.4;

(iii) a RDA at 20 wt. % loading in a range from about 40 to about 200; and (iv) a sphericity factor ($S_{80}$) of greater than or equal to about 0.9.

Aspect 38. Silica particles produced by the process of any one of Aspects 26-37.

Aspect 39. The silica particles of Aspect 38, wherein the silica particles are precipitated silica particles.

Aspect 40. The silica particles of claim 38 or 39, wherein the silica particles are amorphous.

We claim:

1. Silica particles having:
   a d50 median particle size range from about 8.8 to about 15 μm;
   an oil absorption in a range from about 30 to 62 cc/100 g;
   a ratio of (d90−d10)/d50 in a range from about 1.1 to about 2;
   a Relative Dentin Abrasion (RDA) at 20 wt. % loading in a range from about 70 to about 200;
   a sphericity factor ($S_{80}$) of greater than or equal to about 0.9; and
   a pack density in a range of from 52.0 to about 65 lb/ft$^3$; and
   a Pellicle Cleaning Ratio (PCR) at 20 wt. % loading in a range from about 80 to about 110.

2. Silica particles having:
   a d50 median particle size range from about 8.8 to about 15 μm;
   an oil absorption in a range from about 30 to 62 cc/100 g;
   a ratio of (d90−d10)/d50 in a range from about 1.1 to about 2;
   a RDA at 20 wt. % loading in a range from 70 to about 190;
   a sphericity factor ($S_{80}$) of greater than or equal to about 0.92;
   a pack density in a range from 52.0 to about 60 lb/ft$^3$; and
   a Pellicle Cleaning Ratio (PCR) at 20 wt. % loading in a range from about 80 to about 110;
   wherein the silica particles have at least one of the following:
   a BET surface area in a range from about 10 to about 200 m$^2$/g; or
   a 325 mesh residue of less than or equal to about 1.2 wt. %; or
   an Einlehner abrasion value in a range from about 0.5 to about 7 mg lost/100,000 revolutions; or
   the silica particles are precipitated silica particles; or
   the silica particles are amorphous.

3. A composition comprising the silica particles of claim 1.

4. A dentifrice composition comprising the silica particles of claim 1.

5. A dentifrice composition comprising from about 0.5 to about 50 wt. % of the silica particles of claim 1.

6. The dentifrice composition of claim 4, wherein the dentifrice composition further comprises at least one of a humectant, a solvent, a binder, a therapeutic agent, a chelating agent, a thickener other than the silica particles, a surfactant, an abrasive other than the silica particles, a sweetening agent, a colorant, a flavoring agent, and a preservative, or any combination thereof.

7. A process for producing silica particles, the process comprising:
   (a) continuously feeding a mineral acid and an alkali metal silicate into a loop reaction zone comprising a stream of liquid medium, wherein at least a portion of the mineral acid and the alkali metal silicate react to form the silica particles in the liquid medium of the loop reaction zone;
   (b) continuously recirculating the liquid medium through the loop reaction zone, wherein the loop reaction zone does not comprise a stator screen, or the loop reaction zone comprises a stator screen with openings greater than 3 mm$^2$ in cross sectional area, or a shear frequency in the loop reaction zone is less than 1,000,000 interactions/min, or both; and
   (c) continuously discharging from the loop reaction zone a portion of the liquid medium comprising the silica particles,
   wherein the alkali metal silicate is fed into the loop reaction zone as a solution of 20.0 wt. % to 26.6 wt. %, and
   wherein the silica particles produced have;
   a d50 median particle size between about 8.8 and about 20 μm;
   a Pellicle Cleaning Ratio (PCR) at 20 wt. % loading in a range from about 80 to about 110;
   a Relative Dentin Abrasion (RDA) at 20 wt. % loading in a range from about 70 to about 200;
   a sphericity factor ($S_{80}$) of greater than or equal to about 0.9; and
   a pack density in a range from 52.0 to about 65 lb/ft$^3$.

8. The process of claim 7, wherein (a)-(c) are performed simultaneously.

9. The process of claim 7, wherein the loop reaction zone comprises a continuous loop of one or more loop reactor pipes.

10. The process of claim 7, wherein:
the mineral acid and the alkali metal silicate are fed into the loop reaction zone at different points along the loop reaction zone;
the mineral acid comprises sulfuric acid, hydrochloric acid, nitric acid, phosphoric acid, or a combination thereof and is fed into the loop reaction zone as a solution of 17.1 wt. % to 22.8 wt. % mineral acid; and
the alkali metal silicate comprises sodium silicate.

11. The process of claim 7, wherein the liquid medium is recirculated through the loop reaction zone at a pH in a range from about 6 to about 10.

12. The process of claim 7, wherein:
the portion of the liquid medium discharged from the loop reaction zone is discharged at a volumetric rate proportional to an amount of the mineral acid and the alkali metal silicate fed into the loop reaction zone; and
(a)-(c) are performed in a continuous single loop reactor.

13. The process of claim 7, wherein the liquid medium is recirculated through the loop reaction zone at a rate in a range from about 15 L/min to about 150 L/min.

14. The process of claim 7, wherein the liquid medium is recirculated through the loop reaction zone at a rate ranging from about 50 vol. % per minute to about 1000 vol. % per minute.

15. The process of claim 7, wherein greater than 95 wt. % of the liquid medium is recirculated in (b).

16. The process of claim 7, wherein (b) is conducted at a temperature in a range from about 85 to about 100° C.

17. The process of claim 7, further comprising adjusting a pH after (c), filtering after (c), washing after (c), drying after (c), or any combination thereof.

18. The process of claim 7, wherein the silica particles have:
a d50 median particle size between about 8.8 and about 15 μm;
a ratio of (d90−d10)/d50 in a range from about 1.1 to about 2; and
a Relative Dentin Abrasion (RDA) at 20 wt. % loading in a range from about 85 to about 200.

19. Silica particles produced by the process of claim 7, wherein the silica particles have:
a d50 median particle size between about 8.8 and about 15 μm; and
a ratio of (d90−d10)/d50 in a range from about 1.1 to about 2.

20. The silica particles of claim 19, wherein the silica particles are precipitated silica particles.

21. The silica particles of claim 19, wherein the silica particles are amorphous.

* * * * *